United States Patent
Kato

(10) Patent No.: US 8,845,551 B2
(45) Date of Patent: Sep. 30, 2014

(54) MEDICAL GUIDE WIRE, AN ASSEMBLY OF MICROCATHETER AND GUIDING CATHETER COMBINED WITH THE MEDICAL GUIDE WIRE, AND AN ASSEMBLY OF BALLOONCATHETER AND GUIDING CATHETER COMBINED WITH THE MEDICAL GUIDE WIRE

(75) Inventor: Tomihisa Kato, Aichi (JP)

(73) Assignee: Asahi Intecc Co., Ltd., Nagoya (JP)

(*) Notice: Subject to any disclaimer, the term of this patent is extended or adjusted under 35 U.S.C. 154(b) by 639 days.

(21) Appl. No.: 13/171,978

(22) Filed: Jun. 29, 2011

(65) Prior Publication Data

US 2012/0123329 A1 May 17, 2012

(30) Foreign Application Priority Data

Jun. 30, 2010 (JP) .................... 2010-148574

(51) Int. Cl.
A61B 5/00 (2006.01)
(52) U.S. Cl.
USPC ........................................................ 600/585
(58) Field of Classification Search
USPC ......................................................... 600/585
See application file for complete search history.

(56) References Cited

U.S. PATENT DOCUMENTS

| | | | |
|---|---|---|---|
| 4,538,622 A | | 9/1985 | Samson et al. |
| 5,460,187 A | * | 10/1995 | Daigle et al. ............... 600/585 |
| 5,465,732 A | * | 11/1995 | Abele ......................... 600/585 |
| 5,951,496 A | | 9/1999 | Willi |
| 6,325,766 B1 | * | 12/2001 | Anderson et al. ............ 600/585 |
| 7,399,283 B2 | * | 7/2008 | Kato ............................ 600/585 |
| 8,337,519 B2 | * | 12/2012 | Wasicek ...................... 606/200 |
| 2008/0171217 A1 | | 7/2008 | Mishima |
| 2008/0281396 A1 | | 11/2008 | Ishida et al. |

FOREIGN PATENT DOCUMENTS

| | | |
|---|---|---|
| EP | 1731241 A1 | 12/2006 |
| EP | 2269684 A1 | 1/2011 |
| JP | 4-25024 B | 4/1992 |
| JP | 2004-194768 | 7/2004 |
| JP | 2006-297152 | 11/2006 |
| WO | 01/41859 A2 | 6/2001 |

OTHER PUBLICATIONS

Extended European Search Report issued in corresponding European Patent Application No. 11171040.6 dated Oct. 10, 2011.
Notice of Communication issued by the European Patent Office in corresponding European Patent Application No. 11171040.6 dated Feb. 20, 2013.
Notice of Communication issued by the European Patent Office in corresponding European Patent Application No. 11171040.6 dated Jan. 21, 2014.

* cited by examiner

Primary Examiner — Max Hindenburg
(74) Attorney, Agent, or Firm — Morgan, Lewis & Bockius LLP

(57) ABSTRACT

In a medical guide wire 1, a helical spring body 3 is made of austenitic stainless steel wire treated with a solid-solution procedure, and tightly drawn with a whole cross sectional reduction ratio as 90%-99.5%. A metallic wire element of the helical spring body 3 is heat treated at low temperature within a range in which a tensile rupture strength of the helical spring body 3 rapidly increases by partly or totally making use of a conductive heat generated when a core wire 2 and the helical spring body 3 are in part bonded by means of a welding member 4. This makes it possible to improve a mechanical strength property, especially a fatigue-resistant property against a repetitive bending action of the helical spring body 3.

12 Claims, 13 Drawing Sheets

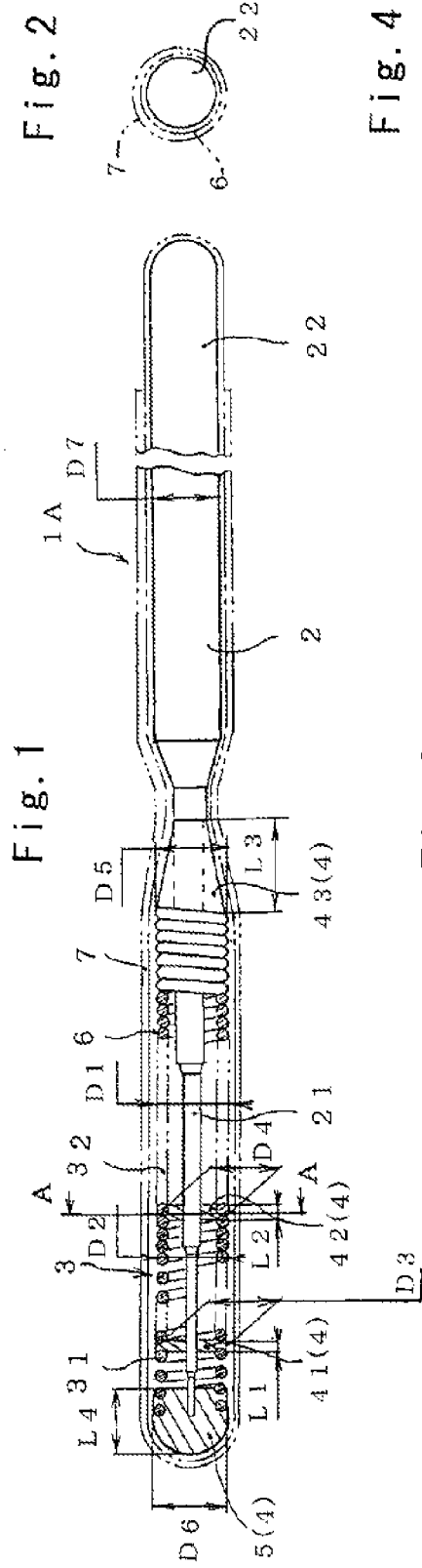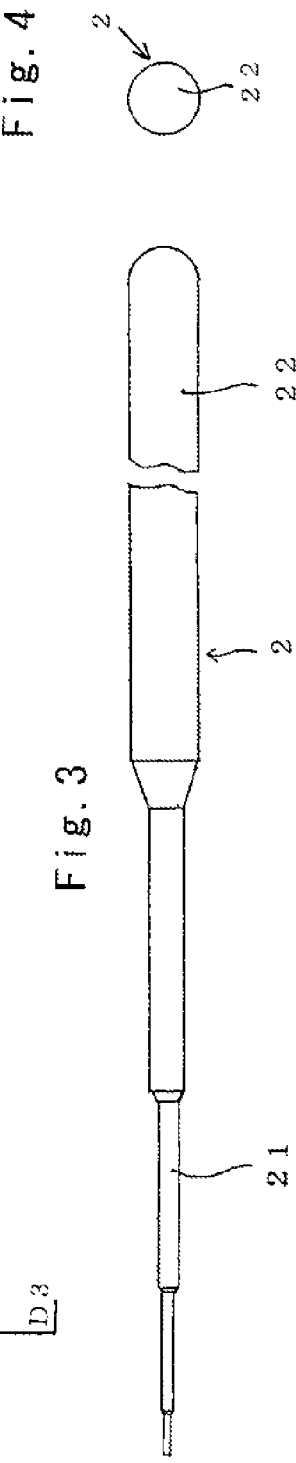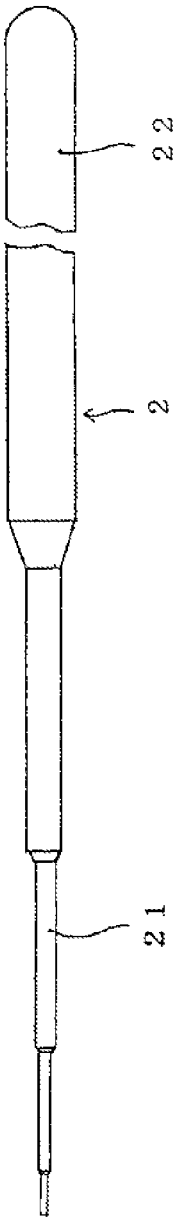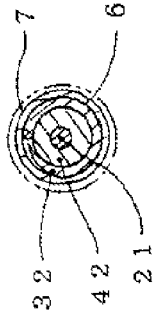

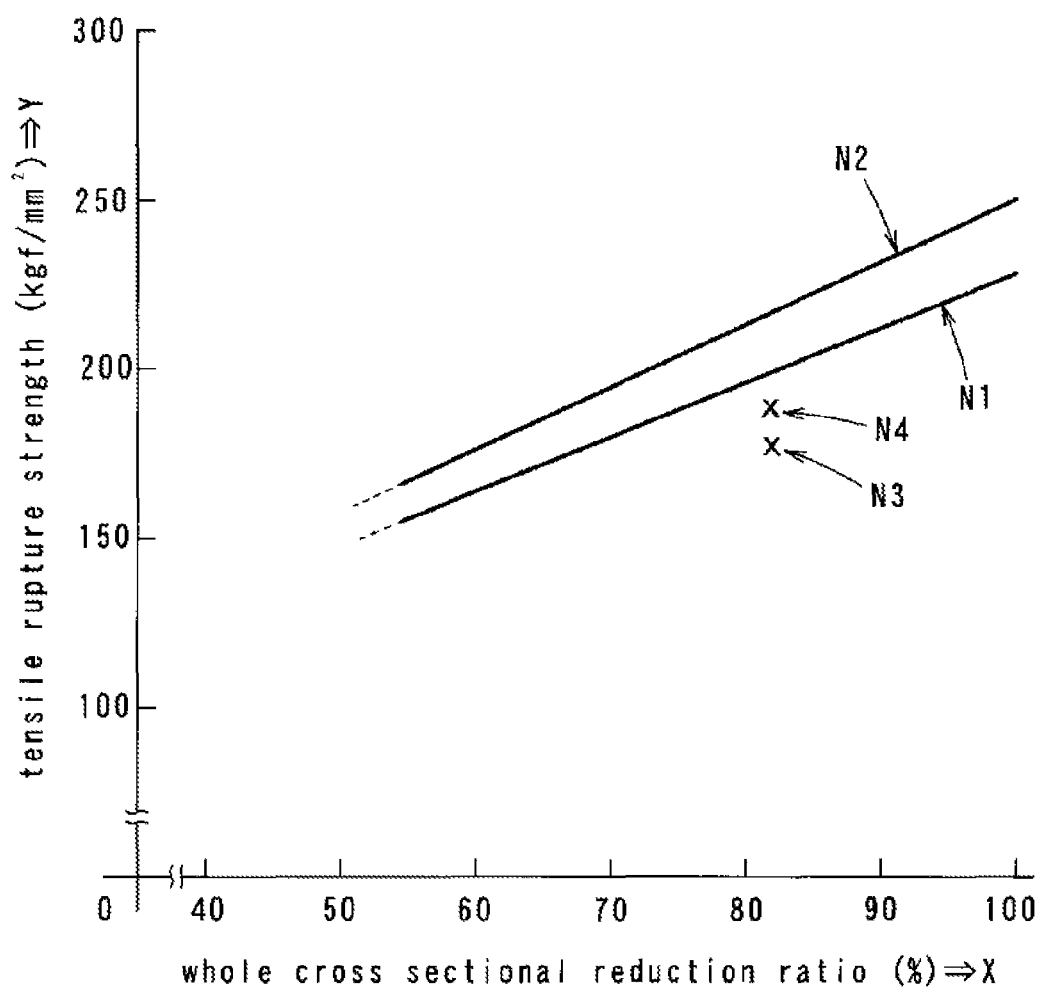

E-E Cross Section

F-F Cross Section

G-G Cross Section

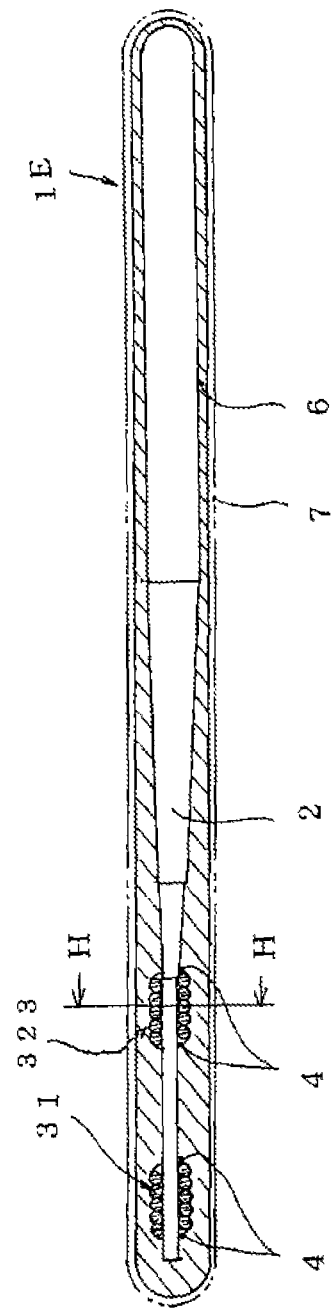
Fig. 17
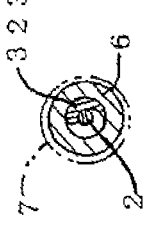
Fig. 18  H-H Cross Section

I-I Cross Section

Fig. 24
Fig. 25
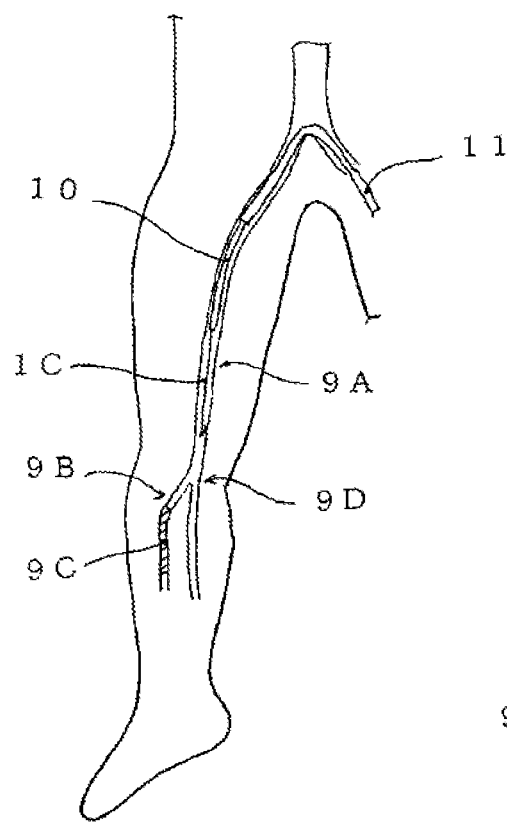
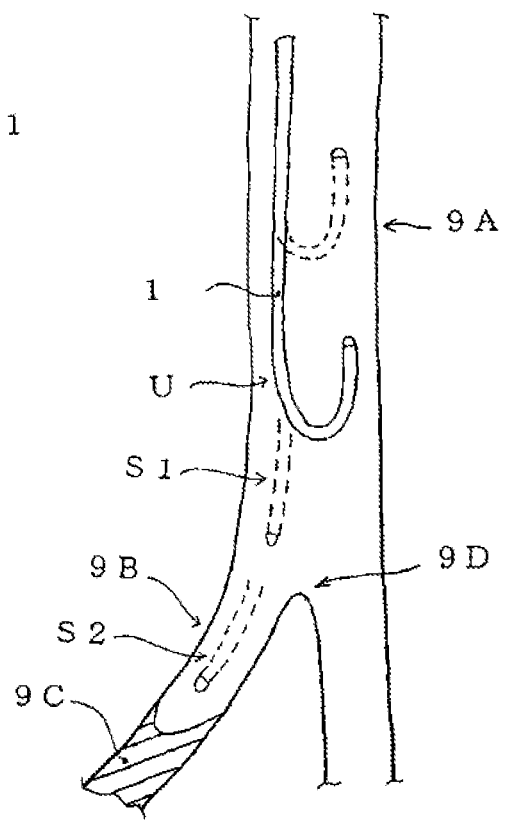

MEDICAL GUIDE WIRE, AN ASSEMBLY OF MICROCATHETER AND GUIDING CATHETER COMBINED WITH THE MEDICAL GUIDE WIRE, AND AN ASSEMBLY OF BALLOONCATHETER AND GUIDING CATHETER COMBINED WITH THE MEDICAL GUIDE WIRE

BACKGROUND OF THE INVENTION

1. Field of the Invention

The present invention relates to a medical guide wire in which a metallic wire element of a helical spring body is improved at its mechanical strength properties by bonding a core wire to the helical spring body by means of a welding member.

2. Description of Related Art

In general, a medical guide wire (referred to simply as a guide wire) is thinned so that the guide wire is inserted into a somatic vasculature. With the thinned wire in mind, it is necessary to impart mechanical requirements to the guide wire with safety measures secured for a human body. For this purpose, various types of contrivances have been introduced.

In Japanese Pre-grant Patent Publication No. 4-25024 (referred to as a first reference hereinafter), the first reference discloses a medical guide wire in which a helical spring body has a radiotransparent coil and a radiopaque coil each connected at a distal end portion of a core wire by screwing the radiotransparent coil into the radiopaque coil. The screwed portion is bonded to the core wire by means of a soldering procedure. This makes it possible to bond members of different material like the case of bonding the radiotransparent coil to the radiopaque coil, while at the same time, ameliorating a visual recognition of the radiopaque coil under the fluoroscopic procedure.

The first reference, however, remains silent about a welding structure which suggests or teaches a correlation between the soldering material and mechanical strength properties of the metallic wire element of the helical spring body.

In Japanese Laid-open Patent Application No. 2004-194768 (referred to as a second reference hereinafter), the second reference discloses a medical guide wire having a core wire which has a mechanical strength (torsional rigidity) of more than 2800 MPa in order to improve a torque transmissibility. The core wire is made of stainless steel containing a high proportion of a silicic component which is different from the stainless steel represented by SUS304, SUS316 or the equivalent.

In Japanese Laid-open Patent Application No. 2006-297152 (referred to as a third reference hereinafter), the third reference discloses a connection structure in which a guide wire has a first coiled wire made of a thickened wire and a second coiled wire made of a thinned wire. The first coiled wire and the second coiled wire are bonded by means of a brazing procedure or the equivalent in order to render a brazing portion to curve evenly between the first coiled wire and the second coiled wire at the time of bending a flexible shaft.

As the case with the first reference, the third reference, however, remains silent about a welding structure which suggests or teaches a correlation between the soldering material and mechanical strength properties of the metallic wire element of the helical spring body. Let alone, the third reference shows no concrete measure to improve the mechanical strength properties of the welded portion between the core wire and the helical spring body by utilizing the melting heat produced upon soldering the core wire to the helical spring body.

In the prior medical guide wires, no technological idea has been introduced that a metallic wire element of a helical spring body (stainless steel wire) is highly drawn by means of a tightly drawing procedure to produce a highly drawn metallic wire element, and a eutectic alloy is used as a welding member (soldering or brazing material) with the thermal influence against the mechanical strength properties taken into consideration so as to improve a tensile rupture strength of the metallic wire element.

No technological idea has been made to utilize a melting heat produced when forming a synthetic resin layer on an outer surface of the helical spring body when the melting heat is conveyed as heat conduction to the helical spring body to improve the tensile rupture strength of the metallic wire element.

Further, no technological idea has been introduced so far to repetitively implement procedure (accumulating procedures) to successively improve the tensile rupture strength by observing a tensile rupture strength property due to the thermal influence against the metallic wire element, so as to impart the metallic wire element with a high tensile rupture strength. Much less, there has been no technological conception strived to concentrically place an inner helical spring body within the helical spring body so as to improve the tensile rupture strength of their metallic wire elements by utilizing the melting heat of the welding member.

Therefore, the present invention has been made with the above situation in mind, it is a main object of the invention to provide a medical guide wire which uses an austenitic stainless steel wire highly drawn as a helical spring body to improve its tensile rupture strength by utilizing the thermal influence given to the metallic wire element when it is highly drawn at the wire-drawing procedure, and further utilizing the thermal influence given by the welding member to improve the tensile rupture strength of the helical spring body which is formed by the metallic wire element.

It is another object of the invention to provide a medical guide wire which is capable to improve the tensile rupture strength of the helical spring body to impart the helical spring body with a fatigue-resistant property so as to enable an operator to use the helical spring body safely.

SUMMARY OF THE INVENTION

According to the present invention, there is provided a medical guide which has a wire formed by a flexible elongate member, and the core wire is inserted to a helical spring body made of a radiotransparent coil. The radiotransparent coil is made by a metallic wire element wound in a spiral fashion.

The metallic wire element is made of an austenitic stainless steel wire which is treated with a solid-solution procedure, and drawn by a wire-drawing procedure with a whole cross sectional reduction ratio as 90%-99.5%. The solid-solution procedure means to form a uniform solid phase by evenly melting two or more metallic components.

The welding member is made of a eutectic alloy having a melting temperature of 180° C.-495° C. including a eutectic alloy having a melting temperature of 180° C.-525° C. when the metallic wire element of the radiotransparent coil contains molybdenum as a component element of the austenitic stainless steel wire. The core wire and the radiotransparent coil are in part bonded by means of the welding means.

With the structure as mentioned above, due to the tensile rupture strength improved by heat treating the highly drawn austenitic stainless steel wire at low temperature, it is possible to improve the tensile rupture strength of the metallic wire element of the radiotransparent coil. The metallic wire element is finally drawn and wound in the spiral fashion to form the helical coil body which is bonded in part to the core wire by means of the welding member. The welding member has the melting temperature, a range of which makes the tensile rupture strength of the metallic wire element rapidly increase, thereby ameliorating the fatigue-resistant property of the helical spring body at a bonded portion in which the helical spring body is bonded to the core wire so as to enable an operator to use the medical guide wire safely.

According to other aspect of the present invention, a distal end side of the helical spring body has a radiopaque coil and a proximal end side of the helical spring body has a radiotransparent coil with a distal end portion of the core wire inserted into the helical spring body. A metallic wire element of the radiotransparent coil is made of an austenitic stainless steel wire treated with the solid-solution procedure, and drawn until the whole cross sectional reduction ratio comes to 90%-99.5% with a predetermined tensile rupture strength. A relationship between X and Y is defined as $Y \geq 1.555X+70$. Where X (%) is the whole cross sectional reduction ratio, and Y ($kgf/mm^2$) is the tensile rupture strength represented by Rp=P1/Sp. Where P1 is a magnitude of a tensile force applied, and Sp is a cross sectional area of the metallic wire element when the metallic wire element surrenders to disconnection.

The structure is such that the relationship between X and Y is defined as $Y \geq 1.555X+70$. After winding the metallic wire element into the helical spring body, the helical spring body is bonded to the core wire by means of the welding member which has the melting temperature, a range of which makes the tensile rupture strength of the metallic wire element rapidly increase, thereby ameliorating the fatigue-resistant property of the helical spring body at a bonded portion of the helical spring body in which the helical spring body is bonded to the core wire.

According to other aspect of the present invention, the metallic wire element of the radiotransparent coil is made of an austenitic stainless steel wire treated with the solid-solution procedure, and drawn by means of a wire-drawing procedure to be heat treated thereafter at low temperature of 300° C.-495° C. or heat treated at low temperature of 300° C.-525° C. when the metallic wire element of the radiotransparent coil contains molybdenum as a component element of the austenitic stainless steel wire. The metallic wire element is finally drawn after implementing at least one set or more with a combination of the wire-drawing procedure and the heat treatment at low temperature as a single one set. The metallic wire element has the whole cross sectional reduction ratio as 90%-99.5% after finally drawn. A total increment of tensile rupture strength is 8% or more due to the heat treatment at low temperature after finally drawn. A relationship between X and Y is defined as $Y \geq 1.777X+70$.

Such is the structure that the metallic wire element is drawn and heat treated at low temperature, a range of which makes the tensile rupture strength rapidly increase, or the metallic wire element is repetitively subjected to the above procedure so as to facilitate the martensitic transformation conducive to improve the tensile rupture strength, thereby imparting the metallic wire element with a high tensile rupture strength represented by the preceding formula. After winding the metallic wire element into the helical spring body (radiotransparent coil), the helical spring body is bonded in part to the core wire with the use of the welding member which has the melting temperature, a range of which makes the tensile rupture strength of the metallic wire element rapidly increase upon heat treating the helical spring body in low temperature.

This makes it possible to disperse a concentrated stress locally occurred on the bonded portion when forming the metallic wire element into the helical spring body, thus homogenizing the texture of the helical spring body so as to additionally improve the fatigue-resistant property at the bonded portion of the helical spring body against the repetitive bending action.

According to other aspect of the present invention, the metallic wire element of the radiotransparent coil is made of a re-melted austenitic stainless steel wire.

Such is the structure that it becomes possible to further draw the metallic wire element readily even after the metallic wire element is highly drawn to have 90% or more as the whole cross sectional reduction ratio, and thinned to have 0.080 mm or less in thickness (or very thinned to have 0.050 mm or less in thickness).

After forming the metallic wire element into the helical spring body, the helical spring body is heat treated in low temperature to improve the tensile rupture strength so as to increase the bonding strength against the core wire. This makes it possible to provide a medical guide wire having the radiotransparent coil made from the metallic wire element with a high tensile rupture strength.

According to other aspect of the present invention, the eutectic alloy of the welding member is an alloy of 80% gold and 20% tin by weight with a melting temperature as 280° C. or an alloy of 3.5% silver and 96.5% tin by weight with a melting temperature as 221° C.

Such is the structure that after forming the metallic wire element into the helical spring body to have the whole cross sectional reduction ratio as 90% or more, the helical spring body is heat treated in low temperature by melting the welding member having a melting temperature, a range of which rapidly increases the tensile rupture strength of the metallic wire element.

This makes it possible to improve the tensile rupture strength of the helical spring body at the bonded portion, while at the same time, increasing the bonding strength of the helical spring body against the core wire.

With the use of the gold metal as the eutectic alloy for the welding member, it is possible to prevent the silver sulfide from developing on the bonded portion so as to avoid the corrosion of the bonded portion due to the darkening phenomenon, so as to maintain its good bonding strength for an extended period of time.

According to other aspect of the present invention, the core wire and the radiotransparent coil are bonded in part by means of the welding member to form a bonded portion in which one doughnut-shaped ring body or a plurality of doughnut-shaped ring bodies are provided from the distal end side to the proximal end side of the helical spring body with an outer diameter of the doughnut-shaped ring body ranging from 0.228 mm to 0.480 mm with a thickness ranging from 0.3 mm to 1.5 mm. Otherwise, one doughnut-shaped ring body is provided at a proximal end portion of the helical spring body with an outer diameter of the doughnut-shaped ring body ranging from 0.228 mm to 0.480 mm with a thickness ranging from 0.3 mm to 3.0 mm, or a cone-shaped body is provided in a tapered-off fashion at the proximal end side of the helical spring body.

Such is the structure that after drawing the metallic wire element to form the helical spring body, it is possible to form the radiotransparent coil, a part or any desired part of which is improved at the tensile rupture strength with the use of the welding member having a melting temperature, a range of which rapidly increases the tensile rupture strength of the metallic wire element.

It is possible to dimensionally measure a length of a stenotic portion of the vasculature under the fluoroscopic operation by arranging the plurality of welding members (containing a gold component as a radiopaque substance) at regular intervals, in arithmetic or geometric progression.

According to other aspect of the present invention, an inner helical spring body is concentrically provided between the core wire and the helical spring body. The inner helical spring body is made of the radiotransparent coil diametrically reduced. The inner helical spring body is made from a plurality of the metallic wire elements stranded to form a wire-twisted hollow body. The core wire is bonded to the helical spring body or the inner helical spring body by means of the welding member to form a bonded portion in which a torus-shaped body or doughnut-shaped ring body is provided from the distal end side to the proximal end side of the helical spring body or the inner helical spring body with an outer diameter of the torus-shaped body or the doughnut-shaped ring body ranging from 0.228 mm to 0.480 mm with a thickness ranging from 0.3 mm to 1.5 mm.

Such is the structure that the helical spring body forms a multi-layered construction with the inner helical spring body placed in the concentric relationship with the helical spring body. With the use of the melting heat of the welding member in the multi-layered construction, it is possible to bond the helical spring body or the inner helical spring body to the core wire, while at the same time, improving the tensile rupture strength of the metallic wire element of the helical spring body or the inner helical spring body, and ameliorating the fatigue-resistant property against the repetitive bending action.

Due to the multi-layered construction, it is possible to quickly reinstate the helical spring body to the original linear-configuration after bending it into a U-shaped configuration, and remarkably ameliorating the torque transmissibility from the proximal end portion to the distal end portion of the medical guide wire.

According to other aspect of the present invention, the helical spring body is heat treated at low temperature to form a synthetic resin layer on an outer surface of the helical spring body at the temperature of 180° C.-450° C. so as to generate a predetermined amount of conductive heat.

The predetermined amount of conductive heat is conveyed from the synthetic resin layer to the metallic wire element of the radiotransparent coil. The synthetic resin layer has $2.5 \times 10^{-4}$ {cal/(cm·sec·° C.)} or more as a thermal conductivity at normal temperature. The metallic wire element has 15 ($W \cdot m^{-1} \cdot K^{-1}$) or more as a heat conductivity at normal temperature with the whole cross sectional reduction ratio as 90%-99.5%.

Such is the structure that after forming the metallic wire element into the radiotransparent coil, the radiotransparent coil is heat treated at low temperature, a range of which makes the tensile rupture strength rapidly increase with the use of melting heat generated from the synthetic resin layer when applying the synthetic resin layer to the outer surface of the radiotransparent coil.

This makes it possible to fully disperse a concentrated stress locally occurred on the bonded portion when forming the metallic wire element into the helical spring body, thereby homogenizing the texture of the helical spring body so as to additionally improve the fatigue-resistant property at the bonded portion of the helical spring body against the repetitive bending action.

According to other aspect of the present invention, the helical spring body is heat treated at low temperature to generate a predetermined amount of conductive heat from the welding member melted when the core wire and the helical spring body are in part bonded, while forming a synthetic resin layer on an outer surface of the helical spring body at the temperature of 180° C.-450° C. so as to generate a predetermined amount of conductive heat. The predetermined amount of conductive heat is conveyed from the synthetic resin layer and the eutectic alloy of the welding member to the metallic wire element of the radiotransparent coil. The eutectic alloy has 63 ($W \cdot m^{-1} \cdot K^{-1}$) or more as a heat conductivity at normal temperature. The synthetic resin layer has $2.5 \times 10^{-4}$ {cal/(cm·sec·° C.)} or more as a thermal conductivity at normal temperature. The metallic wire element has 15 ($W \cdot m^{-1} \cdot K^{-1}$) or more as a heat conductivity at normal temperature with the whole cross sectional reduction ratio as 90%-99.5%.

Such is the structure that after forming the metallic wire element into the radiotransparent coil, the radiotransparent coil is heat treated at low temperature, a range of which makes the tensile rupture strength rapidly increase with the use of melting heat generated from the synthetic resin layer when applying the synthetic resin layer to the outer surface of the radiotransparent coil. At the same time, the radiotransparent coil is heat treated at low temperature, a range of which makes the tensile rupture strength rapidly increase with the use of melting heat generated when the welding member is melted.

With the use of conduction heat concurrently conveyed to the helical spring body when the synthetic resin layer and the welding member are melted, it is possible to fully disperse a concentrated stress locally occurred on the bonded portion when forming the metallic wire element into the helical spring body, thereby homogenizing the texture of the helical spring body so as to additionally improve the fatigue-resistant property at the bonded portion of the helical spring body against the repetitive bending action.

According to other aspect of the present invention, a distal end side of the helical spring body has a radiopaque coil and a proximal end side of the helical spring body has a radiotransparent coil. The helical spring body is heat treated to generate a predetermined amount of conductive heat due to a melting heat concurrently produced when the radiopaque coil and the radiotransparent coil are in part bonded, while forming a synthetic resin layer on an outer surface of the helical spring body at the temperature of 180° C.-450° C. so as to generate a predetermined amount of conductive heat. The predetermined amount of conductive heat is conveyed from the eutectic alloy of the welding member, the synthetic resin layer and the radiopaque coil to the metallic wire element of the radiotransparent coil. The eutectic alloy has 63 ($W \cdot m^{-1} \cdot K^{-1}$) or more as a heat conductivity at normal temperature. The synthetic resin layer has $2.5 \times 10^{-4}$ {cal/(cm·sec·° C.)} or more as a thermal conductivity at normal temperature. The radiopaque coil has a heat conductivity four times or more than that of the radiotransparent coil at normal temperature. The metallic wire element has 15 ($W \cdot m^{-1} \cdot K^{-1}$) or more as a heat conductivity at normal temperature with the whole cross sectional reduction ratio as 90%-99.5%.

Such is the structure that after forming the metallic wire element into the radiopaque coil and the radiotransparent coil, the welding member has the melting temperature, a range of which rapidly increases the tensile rupture strength of the metallic wire element. The synthetic resin layer has the melting temperature, a range of which rapidly increases the tensile rupture strength of the metallic wire element when applying the synthetic resin layer to the outer surface of the helical spring body. The welding member and the synthetic resin layer have the melting heat as first and second conduction heat when they are at the melting temperature.

Further, the melting heat is generated as a third conduction heat at the bonded portion in which the radiopaque coil and the radiotransparent coil are bonded by means of the welding member, and when the melted synthetic resin layer is applied to the outer surface of the helical spring body. The melting heat has at least three types of thermal transference as the first, second and third conduction heat and is concurrently conveyed from the radiopaque coil to the radiotransparent coil to heat treat the radiotransparent coil in low temperature.

This makes it possible to fully disperse a concentrated stress locally occurred when forming the metallic wire element into the helical spring body, thus entirely homogenizing the bonded portion and the helical spring body so as to all the more improve the fatigue-resistant property of the helical spring body against the repetitive bending action.

According to other aspect of the present invention, there is provided an assembly of a microcatheter and a guiding catheter combined with the medical guide wire. An outer diameter of the medical guide wire measures 0.228 mm-0.457 mm (0.009 inches-0.018 inches) which is inserted into the microcatheter, an inner diameter of which measures 0.28 mm-0.90 mm. The medical guide wire inserted into the microcatheter is further inserted into the guiding catheter, an inner diameter of which ranges 1.91 mm to 2.67 mm. The microcatheter forms a helical tube body provided by alternately winding or stranding a plurality of thick wires and thin wires, so that the helical tube body forms a concave-convex portion at an outer surface of the thick wires and the thin wires at least within 300 mm from a distal end of the helical tube body due to an exterior pressure or a pushing force at the time of inserting the helical tube body into a diseased area within a somatic cavity.

Such is the structure that it becomes possible to increase the welding strength at the welded portion between the core wire and the helical spring body, so as to reduce the lengthwise dimension and diametrically minimize the head plug. This leads to rendering the assembly diametrically small, and imparting the microcatheter with a propelling force due to the concave-convex portion, thus realizing a minimally invasive surgery remarkably conducive to the therapeutical treatment against an obstructed portion of the vasculature.

According to other aspect of the present invention, there is provided an assembly of a balloon catheter and a guiding catheter combined with the medical guide wire. An outer diameter of the medical guide wire measures 0.228 mm-0.254 mm (0.009 inches-0.018 inches) which is inserted into the balloon catheter, an inner diameter of which measures 0.28 mm-0.90 mm, and two pairs of the medical guide wire and the balloon catheter are inserted into the guiding catheter, an inner diameter of which measure 1.91 mm-2.67 mm so as to enable a user to readily handle a kissing operation.

With the use of the melting heat of the welding member and the melting heat of the synthetic resin layer, it is possible to provide a medical guide wire which has the helical spring body made from the metallic wire element, the tensile rupture strength of which is sufficiently improved.

On the other hand, the medical guide wire has a thinned wire and exerts a strong propelling force, and the balloon catheter has a highly distensible function. The guiding catheter has a function to support a reactionary force from the two pairs of the medical guide wire and the balloon catheter. The two pairs of the medical guide wire and the balloon catheter are inserted into the guiding catheter to form the assembly to contribute to the therapeutical treatment against a diseased area near the branched portion of the vasculature.

BRIEF DESCRIPTION OF THE DRAWINGS

A preferred form of the present invention is illustrated in the accompanying drawings in which:

FIG. 1 is a longitudinal cross sectional view of a medical guide wire according to a first embodiment of the invention;

FIG. 2 is a right side elevational view of the medical guide wire;

FIG. 3 is a plan view of a core wire;

FIG. 4 is a right side elevational view of the core wire;

FIG. 5 is a latitudinal cross sectional view taken along the line A-A of FIG. 1;

FIG. 6 is a perspective view showing a distal end portion of the core wire;

FIG. 9 is a graphical representation of a tensile strength characteristics showing a relationship between the whole cross sectional reduction ratio and the tensile rupture strength;

FIG. 17 is a longitudinal cross sectional view of a medical guide wire according to a fifth embodiment of the invention;

FIG. 18 is a latitudinal cross sectional view taken along the line H-H of FIG. 17;

FIGS. 24 and 25 are schematic views each showing how to therapeutically treat a diseased area of the blood vessel of the lower limb.

DETAILED DESCRIPTION OF PREFERRED EMBODIMENTS

Figure 7:
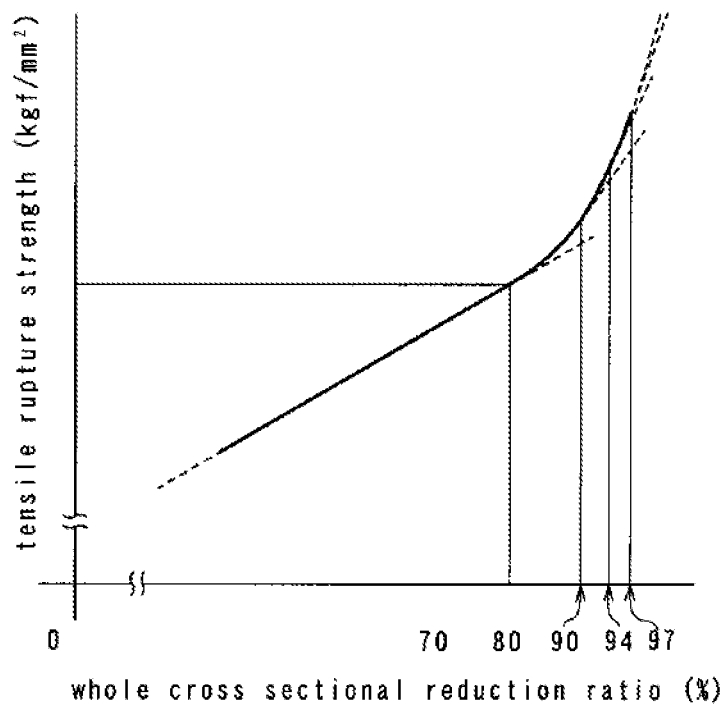
FIG. 7 is a graphical representation showing a relationship between a whole cross sectional reduction ratio and a tensile rupture strength.

In the following description of the depicted embodiments, the like reference numerals are used for features of the same type.

Referring to FIGS. 1 through 6 which show a medical guide wire 1A according to a first embodiment of the invention, the guide wire 1A has a core wire 2 formed by a flexible elongate member. The core wire 2 has a distal end portion 21, around which a helical spring body 3 is coaxially placed as shown in FIGS. 1 through 5.

The helical spring body 3 has a distal end portion as a radiopaque coil 31 which is made of a metallic wire element (referred to simply as metallic wire hereinafter) such, as silver, platinum, wolfram wire or the equivalent. The helical spring body 3 has a proximal end portion as a radiotransparent coil 32 which is formed by winding a stainless steel wire around the core wire 2. The metallic wire of the radiopaque coil 31 and the stainless steel wire of the radiotransparent coil 32 have a diameter within a range of 0.050 mm-0.095 mm.

At a distal end portion 21 of the core wire 2, an intermediate front weld portion 41, an intermediate rear weld portion 42 and a rear side weld portion 43 are provided. The radiopaque coil 31 and the radiotransparent coil 32 are bonded in part to the core wire 2 by means of the intermediate front weld portion 41, the intermediate rear weld portion 42 and the rear side weld portion 43 with the use of a welding member 4.

To a distal extremity of the core wire 2, a head plug 5 is bonded by means of the welding member 4. The head plug 5 has a rounded tip and a columnar neck, around the latter of which a distal end of the radiopaque coil 31 encircles to connectedly bond the radiopaque coil 31 to a distal end of the core wire 2.

At the intermediate front weld portion 41, a rear end of the radiopaque coil 31 and a front end of the radiotransparent coil 32 are bonded to concurrently secure the coils 31, 32 to the distal end portion 21 of the core wire 2 by means of the welding member 4.

The radiotransparent coil 32, which is formed by winding the austenitic stainless steel wire, measures 30 mm-300 mm in length with an outer diameter D1 (D2) as 0.356 mm-0.457 mm. The core wire 2 measures 0.060 mm-0.200 mm in diameter as a thinned wire along the distal end portion 21 approximately within a length of 300 mm from the distal extremity end of the core wire 2. The core wire 2 also measures 0.356 mm-0.457 mm in diameter D7 as a thickened wire along the proximal end portion 22 approximately within a length of 1200 mm-2700 mm from the distal extremity end of the core wire 2. The distal end of the core wire 2 is circular in cross section and successively decreases its diameter as approaching distally. The distal end of the core wire 2 may be flattened to be rectangular in cross section as shown in FIG. 6.

Both the core wire 2 and the helical spring body 3 have an outer surface coated by a synthetic resin layer 6 which is formed from polyurethane, fluororesin (e.g., polytetrafluoroethylene (PTFE)) or other polymers. To an outer surface of the synthetic resin layer 6, applied is a hydrophilic film 7 which is formed by polyvinylpyrrolidone or the equivalent to exhibit a lubricant property when moistened. The helical spring body 3 has the outer surface tightly coated by the synthetic resin layer 6 and the hydrophilic film 7 to form a double-layered construction.

The metallic wire of the radiotransparent coil 32 uses the austenitic stainless steel wire treated with the solid-solution procedure, and drawn by means of wire-drawing procedure to have a whole cross sectional reduction ratio as 90%-99.5% with a tensile rupture strength as 200 kgf/mm$^2$ or more. The solid-solution procedure means to form a uniform solid phase by evenly melting two or more metallic components.

The whole cross sectional reduction ratio is represented by percentage based on a cross sectional difference between an original cross sectional area of the metallic wire before subjecting to the wire-drawing procedure and a finished cross sectional area of the final metallic wire after subjecting to the wire-drawing procedures with the use of a plurality of dices.

In this instance, the metallic wire is heat treated at 1050° C. to have 60 kgf/mm$^2$-80 kgf/mm$^2$ as a tensile rupture strength by way of example.

The cross sectional reduction ratio is referred to the metallic wire which is subjected to one or some turns of wire-drawing procedure among predetermined numbers of the wire drawing procedure, while the whole cross sectional reduction ratio is referred to the metallic wire which is subjected to all the wire-drawing procedures among the predetermined numbers of the wire drawing procedure.

The tensile rupture strength is referred to a value obtained by dividing a tensile force by a cross sectional area of the metallic wire when the metallic wire is subjected to the tensile force to be disconnected.

The heat treatment in low temperature is referred to the meaning to increase the mechanical properties so as to improve the tensile rupture strength, contrary to an annealing procedure which softens the steel wire to decrease its hardness and tensile rupture strength. It is also different from the annealing and the normalizing procedure in low temperature, the latter of which heats the steel wire at the temperature (e.g., 730° C. or more at AC3) more than the transformation requires.

The metallic wire is formed by drawing the austenitic stainless steel wire treated with the solid-solution in order to insure the austenitic texture of good machinability. It is difficult to refine the crystallized grains of the austenitic stainless steel with the transformation point as an indication. It becomes possible to refine the crystallized grains by means of cold working procedure. It is found that the wire-drawing procedure exhibits a remarkable work-hardened property on the austenitic stainless steel wire to improve the tensile rupture strength.

The austenitic stainless steel wire is employed to the metallic wire because the martensitic stainless steel wire is susceptible to the thermal influence to exhibit a quench-hardening property due to the heat treatment. The precipitation-hardened stainless steel wire (e.g., SUS630) is susceptible to disconnection due to an insufficiency of toughness when forming it into the helical spring body. The ferro-based stainless steel has the temperature-brittle property (sigma-brittleness).

At the intermediate front weld portion 41 which bonds the helical spring body 3 to the core wire 2 by means of the welding member 4 (brazing, soldering procedure), the rear end of the radiopaque coil 31 is screwed into the front end of the radiotransparent coil 32 so as to form a screwed portion. The screwed portion is bonded to the core wire 2 (0.060 mm-0.150 mm in diameter), while the radiotransparent coil 32 is bonded to the core wire 2 (approximately 0.100 mm-0.200 mm in diameter) at the intermediate rear weld portion 42.

The intermediate front weld portion 41 forms a doughnut- or torus-shaped ring body which measures approximately 0.3 mm-1.5 mm in thickness L1 with an outer diameter D3 approximately as 0.360 mm-0.480 mm. The intermediate rear weld portion 42 also forms a doughnut- or torus-shaped ring body which measures approximately 0.3 mm-1.5 mm in thickness L2 with an outer diameter D3 approximately as 0.360 mm-0.480 mm.

The rear side weld portion 43 forms an annular body or cone-shaped body, the latter of which progressively decreases its diameter as approaching proximally, and measures approximately 0.3 mm-3.0 mm in length L3 with an outer diameter D5 approximately as 0.360 mm-0.480 mm.

The head plug 5 provided by bonding the radiopaque coil 31 to the core wire 2 (approximately 0.060 mm-0.100 mm in diameter) by means of the welding member 4, has approximately 0.2 mm-1.5 mm in length L4 with an outer diameter D6 as approximately 0.360 mm-0.480 mm. The head plug 41 may be formed into a cylindrical, semi-spherical or cone-shaped configuration. The phrase of "bonding something in part by means of the welding member 4" means to bond the weld portions 41, 42, 43 and the head plug 5 against the helical spring body 3 and the core wire 2 with the use of the welding member.

As described hereinafter in detail at sixth to eighth embodiment of the invention (FIGS. 19-23), the present invention includes bonded features when the helical spring body 3 and an inner helical spring body 33 are mutually bonded, and the spring bodies 3, 33 are bonded to the distal end portion 21 of the core wire 2 so as to form a double-layered construction in which the inner helical spring body 33 is concentrically placed between the helical spring body 3 and the distal end portion 21 of the core wire 2. The inner helical spring body 33 is formed from a radiotransparent coil which measures 0.185 mm (0.357 mm or less) in diameter (D11).

In Tables 1, 2 which shows the metallic wire employed to the radiotransparent coil 32 and the inner helical spring body 33, the austenitic stainless steel wire (0.3 mm in diameter, 70 kgf/mm$^2$ in tensile rupture strength) is treated with the solid-solution procedure as a first metallic wire 1e, and primarily drawn to have the whole cross sectional reduction ratio as 90% with the diameter reduced to 0.095 mm (210 kgf/mm$^2$ in tensile rupture strength).

A second metallic wire 1c is primarily drawn to have the whole cross sectional reduction ratio as 94.5% with the diameter reduced to 0.072 mm (221.1 kgf/mm$^2$ in tensile rupture strength). A third metallic wire 1e is produced by primarily heat treating a fourth metallic wire 1d after drawn, and secondarily drawn to have the whole cross sectional reduction ratio as 97.2% with the diameter reduced to 0.051 mm (282.4 kgf/mm$^2$ in tensile rupture strength).

Other metallic wires represented by 1b, 1d, 1f are specimens each subjected to the primary or secondary heat treatment in low temperature after the metallic wires 1a, 1c, 1e are finally drawn (primarily or secondarily) so as to have 235 kgf/mm$^2$-308.9 kgf/mm$^2$ in terms of the tensile rupture strength. A metallic wire represented by 1g is a specimen employed to the inner helical spring body 33. The metallic wire 1g starts from the austenitic stainless steel wire (0.432 mm in diameter) treated with the solid-solution procedure with the tensile rupture strength as 70 kgf/mm$^2$, and drawn to diametrically reduce the metallic wire (0.030 mm in diameter) until the whole cross sectional reduction ratio reaches 99.5% with the tensile rupture strength as 403 kgf/mm$^2$. A first comparative specimen 1 is a metallic wire primarily drawn with the whole cross sectional reduction ratio as 79.8%. A second comparative specimen 2 is produced after primarily heat treating the first comparative specimen 1 in low temperature. To the metallic wires 1a 1d, a starting material represented by SUS304 is employed. To the metallic wires 1e, 1f, a starting material represented by SUS316 is employed with an addition of molybdeum (2%-3% by weight). To the metallic wire 1g, a starting material represented by re-melted SUS316 is employed with an addition of molybdeum (2%-3% by weight).

TABLE 1

| procedures | | metallic wire 1a | metallic wire 1b | metallic wire 1c | metallic wire 1d |
|---|---|---|---|---|---|
| starting wire: diameter | (mm) | 0.3 | 0.3 | 0.307 | 0.307 |
| tensile rupture strength | (kgf/mm$^2$) | 70 | 70 | 70 | 70 |
| primary drawing | | | | | |
| wire diameter | (mm) | 0.095 | 0.095 | 0.072 | 0.072 |
| cross sectional reduction ratio | (%) | 90.0 | 90.0 | 94.5 | 94.5 |
| tensile rupture strength | (kgf/mm$^2$) | 210 | 210 | 221.1 | 221.1 |
| primary heat treating | | | | | |
| temp · time | | | 460° C. · 40 min | | 460° C. · 40 min. |
| tensile rupture strength | (kgf/mm$^2$) | | 235 | | 253.8 |
| increment rate (①) | (%) | | 11.9 | | 14.8 |
| secondary drawing | | | | | |
| wire diameter | (mm) | | | | |
| cross sectional reduction ratio | (%) | | | | |
| tensile rupture strength | (kgf/mm$^2$) | | | | |
| secondary heat treating | | | | | |
| temp · time | | | | | |
| tensile rupture strength | (kgf/mm$^2$) | | | | |
| increment rate (②) | (%) | | | | |
| whole cross sectional reduction ratio | (%) | 90.0 | 90.0 | 94.5 | 94.5 |
| total of increment rate (① + ②) | (%) | — | 11.9 | — | 14.8 |

TABLE 2

| procedures | | metallic wire 1e | metallic wire 1f | metallic wire 1g |
|---|---|---|---|---|
| starting wire diameter | (mm) | 0.307 | 0.307 | 0.432 |
| tensile rupture strength | (kgf/mm$^2$) | 70 | 70 | 70 |
| primary drawing | | | | |
| wire diameter | (mm) | 0.072 | 0.072 | 0.098 |
| cross sectional reduction ratio | (%) | 94.5 | 94.5 | 94.8 |
| tensile rupture strength | (kgf/mm$^2$) | 221.1 | 221.1 | 222.2 |

TABLE 2-continued

| procedures | | metallic wire 1e | metallic wire 1f | metallic wire 1g |
|---|---|---|---|---|
| primary heat treating | | | | |
| temp · time | | 460° C. · 40 min. | 460° C. · 40 min. | 460° C. · 40 min. |
| tensile rupture strength | (kgf/mm²) | 253.8 | 253.8 | 269.1 |
| increment rate (①) | (%) | 14.8 | 14.8 | 21.1 |
| secondary drawing | | | | |
| wire diameter | (mm) | 0.051 | 0.051 | 0.049 |
| cross sectional reduction ratio | (%) | 49.8 | 49.8 | 75.0 |
| tensile rupture strength | (kgf/mm²) | 282.4 | 282.4 | 307.5 |
| secondary heat treating | | | | |
| temp · time | | | 460° C. · 40 min. | 460° C. · 40 min. |
| tensile rupture strength | (kgf/mm²) | | 308.9 | 341.3 |
| increment rate (②) | (%) | | 9.4 | 11.0 |
| tertiary drawing | | | | |
| wire diameter | (mm) | | | 0.030 |
| cross sectional reduction ratio | (%) | | | 62.5 |
| tensile rupture strength | (kgf/mm²) | | | 403 |
| whole cross sectional reduction ratio | (%) | 97.2 | 97.2 | 99.5 |
| total of increment rate (① + ②) | (%) | 14.8 | 24.2 | 32.1 |

TABLE 3

| procedures | | comparative specimen 1 | comparative specimen 2 |
|---|---|---|---|
| starting wire: diameter | (mm) | 0.160 | 0.160 |
| tensile rupture strength | (kgf/mm²) | 70 | 70 |
| primary drawing | | | |
| wire diameter | (mm) | 0.072 | 0.072 |
| cross sectional reduction ratio | (%) | 79.8 | 79.8 |
| tensile rupture strength | (kgf/mm²) | 183 | 183 |
| primary heat treating | | | |
| temp · time | | | 460° C. · 40 min. |
| tensile rupture strength | (kgf/mm²) | | 189 |
| increment rate (①) | (%) | | 3.2 |
| whole cross sectional reduction ratio | (%) | 79.8 | 79.8 |
| total of increment rate (①) | (%) | — | 3.2 |

As shown in Tables 1-3, by primarily heat treating the metallic wires 1b, 1d at 460° C. for 40 minutes, the increment of the tensile rupture strength is approximately 3.7-4.6 times greater than that of the second comparative specimen 2 (79.8% in whole cross-sectional reduction ratio).

The metallic wire 1f (97.2% in whole cross sectional reduction ratio) is produced by secondarily heat treating the metallic wire 1e in low temperature after secondarily drawn. A total increment of the tensile rupture strength comes to 24.2%, i.e., approximately 7.6 times greater than that of the second comparative specimen (79.8% in whole cross sectional reduction ratio).

The metallic wire 1g (99.5% in whole cross sectional reduction ratio) maximizes its tensile rupture strength (403 kgf/mm²) to attain 32.1% as a total increment of the tensile rupture strength, i.e., approximately 10 times greater than that of the second comparative specimen.

FIG. 7 is a graphical representation showing a relationship between the whole cross sectional reduction ratio (%) and the tensile rupture strength (kgf/mm²).

It is found from FIG. 7 that the tensile rupture strength increases as a point of inflection when the whole cross sectional reduction ratio is around 90%, and the tensile rupture strength abruptly increases especially when the whole cross sectional reduction ratio is in the vicinity of 94% and 97%.

As observed above, the tensile rupture strength abruptly increases with the whole cross sectional reduction ratio as 90%-99.5%. The tensile rupture strength additionally increases by secondarily heat treating the metallic wire in low temperature after secondarily drawn. The increment rate of the tensile rupture strength exceeds 8% and reaches over 10%. As a result, the tensile rupture strength exceeds 210 kgf/mm² (400 kgf/mm²), and reaches 235 kgf/mm² (403 kgf/mm²).

For the metallic wire employed to the radiotransparent coil, it is preferable to attain 90%-99.5% in terms of the whole cross sectional reduction ratio. It is further preferable to attain 94%-99.5%, and more preferable to attain 97%-99.5%, and most preferably to attain 97%-99% in terms of the whole cross sectional reduction ratio.

The whole cross sectional reduction ratio is determined to be 90% or more because the point of inflection appears to abruptly increase the whole cross sectional reduction ratio when the whole cross sectional reduction ratio is in the proximity of 80%, 90% or more (refer to Page 63 and Figure Number 2.82 of "Manual on Helical Spring", 3rd Edition Published by Maruzen Inc.).

The whole cross sectional reduction ratio is determined to be 94% or more, otherwise 97%-99.5% because the point of inflection appears to remarkably increase the whole cross sectional reduction ratio. The whole cross sectional reduction ratio is determined to be 99.5% or less because the metallic wire begins to appear minute voids inside the metallic texture, and comes to be susceptible to disconnection due to its brittleness when the reduction ratio exceeds 99.5%.

The whole cross sectional reduction ratio is determined to be 99% as its upper limit value in the most preferable modes because the metallic wire leaves only a little room to be drawn, so that cracks and scale-like pattern may appear on the outer surface of the helical spring body upon forming the metallic wire into the helical spring body when the whole cross sectional reduction ratio exceeds 99%.

The radiotransparent coil 32 may be formed after finally heat treating the metallic wire, however, it is preferable to finally heat treat the radiotransparent coil 32 in low temperature after the metallic wire is finally drawn (primary drawing procedure for the metallic wires 1a, 1c, 1d, secondary drawing procedure for the metallic wire 1f, and tertiary drawing procedure for the metallic wire 1g).

This makes it possible to easily form the radiotransparent coil 32 more than the case in which the metallic wire is finally drawn after finally heat treated in low temperature upon forming the radiotransparent coil 32.

The final heat treatment also prevents the cracks and injuries from occurring on the outer surface of the helical spring body upon forming the metallic wire into the helical spring body, and dispersing the locally concentrated stress to homogenize the texture of the helical spring body, thereby removing the residual stress to impart the helical spring body with the fatigue-resistant property against the repetitive bending action.

As observed from Table 2, the metallic wire is finally drawn after implementing at least one set or more with a combination of the wire-drawing procedure and the heat treatment at low temperature as a single one set. When the metallic wire has the whole cross sectional reduction ratio as 97.2%-99.5% after finally drawn, a total increment rate of the tensile rupture strength comes to 14.8%-32.1%, which is far greater than 8% or more in terms of the tensile rupture strength due to the heat treatment at low temperature after finally drawn.

The metallic wire 1g (0.030 mm in diameter) employed to the inner helical spring body 33 is made from the re-melted metallic material (SUS316) in which the austenitic stainless steel wire contains 2%-3% molybdenum (Mo) by weight.

The metallic wire 1g is made by primarily heat treating a starting wire (0.432 mm in diameter) at 180° C.-525° C. for 10-180 minutes (e.g., 460° C. for 40 minutes) as an atmospheric heating within a furnace after implementing the primarily drawing procedure. Thereafter, the starting wire is secondarily drawn, then secondarily heat treated in low temperature and tertiarily drawn (finally drawn) so as to attain 403 kgf/mm² in terms of the tensile rupture strength with the whole cross sectional reduction ratio as 99.5%.

In order to improve the tensile rupture strength of the metallic wire, it is sufficient to attain 210 kgf/mm² as the tensile rupture strength merely by primarily drawing the starting wire with the cross sectional reduction ratio as 90% or more.

In order to further improve the tensile rupture strength of the metallic wire, it is preferable to implement at least one set or more with the combination of the wire-drawing procedure and the heat treatment at low temperature as a single one set. Otherwise, five sets or more may be implemented, however, it is preferable to implement three sets or less from the manufacturing point of view.

The metallic wires 1a-1g have 90% or more as the whole cross sectional reduction ratio, and defined by the following relationship between X (whole cross sectional reduction ratio) and Y (tensile rupture strength) as shown at N1 in FIG. 9.

$$Y \geq 1.555X + 70 \quad \text{(first formula)}$$

By way of example, the metallic wire 1b has 90% as the whole cross sectional reduction ratio X, and the tensile rupture strength Y is determined to be 209.9 kgf/mm² or more from the first formula. The metallic wire 1b satisfies formula because the metallic wire 1b actually has 235 kgf/mm² as the tensile rupture strength. However, the first and second comparative specimens 1, 2 do not satisfy the first formula as shown at N3, N4 in FIG. 9.

The metallic wire 1d has 90% or more as the whole cross sectional reduction ratio, and subjected to one set with the combination of the wire-drawing procedure and the heat treatment at low temperature as a single one set.

The mechanical strength required for the metallic wire 1d is defined by the following relationship between X (whole cross sectional reduction ratio) and Y (tensile rupture strength) as shown at N2 in FIG. 9.

$$Y \geq 1.777X + 70 \quad \text{(second formula)}$$

The metallic wire 1d has 94.5% as the whole cross sectional reduction ratio X, and the tensile rupture strength Y is determined to be 237.9 kgf/mm² or more from the second formula. The metallic wire 1d satisfies the formula because the metallic wire 1d actually has 253.8 kgf/mm² as the tensile rupture strength Y. However, the second comparative specimen 2 does not satisfy the second formula.

It is preferable to heat treat the metallic wire at 300° C.-495° C. in low temperature, and preferable at 300° C.-525° C. when the metallic wire is made from the austenitic stainless steel wire which contains molybdenum (Mo).

As opposed to the comparative specimens 1, 2, the metallic wires 1a-1g have the tensile rupture strength remarkably improved with the increase of the whole cross sectional reduction ratio.

It is possible to produce the metallic wire of high tensile rupture strength by heat treating the metallic wire in low temperature, range of which rapidly increases the tensile rupture strength (mechanical property) of the metallic wire, and repetitively implementing the sets with the combination of the wire-drawing procedure and the heat treatment at low temperature as a single one set.

The tensile rupture strength of the metallic wire is further improved by selecting not only the type of the stainless steel wire suitable for implementing the tight wire-drawing procedure but also the thermal range suitable for the heat treatment in low temperature.

As observed at the metallic wires 1b, 1d and 1f, the metallic wires increase their tensile rupture strength by being heat treated in low temperature after finally drawn.

In consequence, the total increment rate of the tensile rupture strength for the metallic wires 1b, 1d and 1f comes to 11.9%, 14.8% and 9.4% in turn. This makes it possible to obtain the radiotransparent coil 32 and the inner helical spring body 33 each made of the metallic wire in which the tensile rupture strength exceeds 210 kgf/mm²-400 kgf/mm².

Following are how characteristics of the tensile rupture strength changes depending on types of the austenitic stainless steel wire which are highly drawn under the heat treatment in low temperature.

Figure 8:
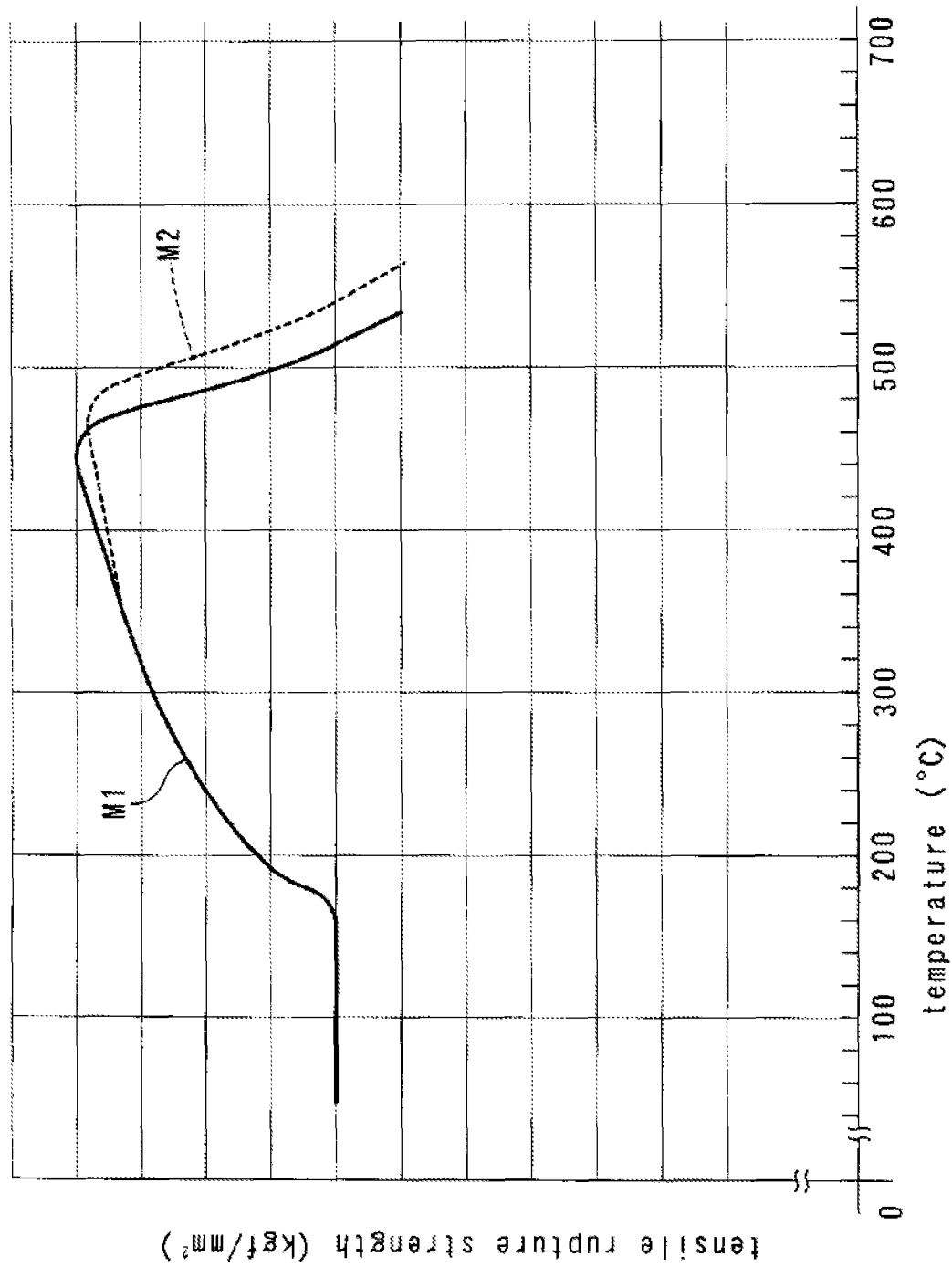
FIG. 8 is a graphical representation showing a relationship between temperature and the tensile rupture strength.

FIG. 8 is a graphical representation showing how the characteristics of the tensile rupture strength changes under the thermal influence (exposed to each temperature for 30 minutes) with the use of the metallic wire finally drawn with the tensile rupture strength as 90% or more.

In FIG. 8, the metallic wire designated by the solid line M1 is based on the first steel-based material (SUS304), and the metallic wire designated by the broken line M2 is based on the second steel-based material (SUS316). The metallic wire M1 begins to gain the tensile rupture strength at around 180° C. and exhibits the maximum tensile rupture strength at around 450° C., and maintains the favorable tensile rupture strength until the temperature reaches 495° C. The tensile rupture strength abruptly descends to be lower than that of the normal temperature (20° C.) when the temperature reaches 520° C. and beyond.

The metallic wire M2 exhibits the same tendency as the metallic wire M1 exhibits at the lower temperature range, and exhibits the maximum tensile rupture strength at around 480° C., and maintains the favorable tensile rupture strength until the temperature reaches 525° C. The tensile rupture strength abruptly descends to be lower than that of the normal temperature (20° C.) when the temperature reaches 540° C. and beyond.

Reasons why the tensile rupture strength abruptly descends are as follows:

The austenitic stainless steel wire decreases its tensile rupture strength significantly since when the austenitic stainless steel wire is heated at the temperature of 800° C. which goes beyond 520° C. and 540° C., it begins to require an energy to precipitate the carbon particles and mobilize chromium within the inside texture of the austenitic stainless steel wire (susceptive phenomenon), so as to exceedingly reduce the tensile rupture strength. Especially for the austenitic stainless steel wire (SUS304) which contains carbon component in less than 0.08%, the susceptive phenomenon appears in less than 4-5 minutes at 700° C.

As a consequence of the above observation, it is preferable to heat treat the metallic wire (SUS304) in low temperature within the range of 180° C.-495° C. in which the metallic wire abruptly increase the tensile rupture strength.

For the metallic wire (SUS316) which contains, for example, such as 2%-3% Mo by weight, it is preferable to heat treat the metallic wire (SUS316) at 180° C.-525° C.

In general, it is preferable to heat treat the metallic wire (SUS304) at 300° C.-495° C., and heat treat the metallic wire (SUS316) at 300° C.-525° C. as observed in FIG. 8.

Based on the characteristics of the tensile rupture strength which the austenitic stainless steel exhibits after highly drawn with a considerable value reached as the whole cross sectional reduction ratio, and by selectively employing the temperature suitable for the types of the stainless steel wire, it is possible to improve the tensile rupture strength of the metallic wire employed to the radiotransparent coil 32 and the inner helical spring body 33, the latter of which is also made of the radiotransparent material.

The austenitic stainless steel wire of the present invention has chemical composition as follows:

C: less than 0.15% by weight, Si: less than 1.0% by weight, Mn: less than 2.0% by weight, Ni: 6%-16% by weight, Cr: 16%-20% by weight, P: less than 0.045% by weight, S: less than 0.030% by weight, Mo: less than 3.0% by weight, balance: iron and impure substances unavoidably contained.

Without using a high silicic stainless steel (Si: 3.0%-5.0% by weight) or the precipitation-hardened stainless steel wire (e.g., SUS630), is possible to provide the core wire 2 with a high tensile strength by means of the austenitic stainless steel wire.

It is preferable to add 0.005% or more as a carbon component to increase the tensile rupture strength, and add 0.15% or less as the carbon component to prevent the intergranular corrosion.

The metallic wire employed to the radiotransparent coil 32 measures 0.050 mm-0.095 mm in diameter, and the metallic wire employed to the inner helical spring body 33 measures 0.010 mm-0.040 mm in diameter.

Especially, it is preferable to use the re-melted material (SUS304) or (SUS316) in order to achieve 220 kgf/mm$^2$ or more as the tensile rupture strength by means of the austenitic stainless steel wire (less than 0.075 mm in diameter) with the whole cross sectional reduction ratio designed to be more than 94%.

The reason why the re-melted material is employed, is that the stainless steel wire is likely to disconnect due to the presence of oxidized substances rather than cracks and injuries occurred on the outer surface of the stainless steel wire. This is all the more true as the metallic wire comes to be thinned.

It is preferable to reduce the chemical components Ti, Al, Ti, Ca and O which are elements of the oxidized substances. This is true with the sulfur which causes to reduce the drawing capability of the stainless steel wire.

With the above matters taken into consideration, the austenitic stainless steel wire needs the chemical composition as follows:

C: less than 0.08% by weight, Si: less than 0.10% by weight, Mn: less than 2.0% by weight, P: less than 0.045% by weight, S: less than 0.10% by weight, Ni: 8%-12% by weight, Cr: 16%-20% by weight, Mo: less than 3.0% by weight, Al: less than 0.0020% by weight, Ti: less than 0.10% by weight, Ca: less than 0.0050% by weight, 0: less than 0.0020% by weight, and balance: iron and impure substances unavoidably contained.

Upon manufacturing the re-melted materials, the flux is used to an ingot of the re-melted stainless steel as the electro-slug re-melting method. The thrice-melted material may be used.

For the welding member 4 which is used to bond the radiotransparent coil 32 and the inner helical spring body 33, it is preferable to have the melting temperature (180° C.-525° C.), a range of which rapidly increases the tensile rupture strength of the metallic wire.

By employing a eutectic alloy to the welding member 4 so that the eutectic alloy melts within the above temperature range (180° C.-525° C.), it becomes possible to improve the tensile rupture strength of the metallic wire at the bonded portion, while at the same time, ameliorating the bonding strength at the bonded portion.

Taking into consideration the characteristics of the tensile rupture strength which the austenitic stainless wire exhibits when highly drawn to have a high tensile rupture strength, the soldering metal and brazing metal are used not only as a bonding element but also as a means to increase the bonding strength while improving the tensile rupture strength of the metallic wire.

The eutectic alloy means a special alloyed metal, components of which can be adjusted to gain a lowest melting point (melting temperature). Employed to the welding member 4 is the eutectic alloy which has 180° C.-495° C. as the melting temperature. Employed to the metallic wire is the eutectic alloy which has 180° C.-525° C. as the melting temperature when the metallic wire contains molybdeum (Mo) as the component of the austenitic stainless steel wire.

As a gold-tin based alloy, it contains 80% gold by weight and 20% tin by weight to have the melting temperature 280° C. As a silver-tin based alloy, it contains 3.5% silver by weight and 96.5% tin by weight to have the melting temperature of 221° C. As a gold-germanium based alloy, it contains 88% gold by weight and 12% germanium by weight to have the melting temperature of 356° C. As gold-tin-indium based alloys, they are represented to have the melting temperature of 450° C.-472° C. as shown in Table 4.

TABLE 4

| No. | eutectic alloy (%) by weight | melting temp. |
| --- | --- | --- |
| A-1 | gold (80%) tin (20%) | 280° C. |
| A-2 | gold (10%) tin (90%) | 217° C. |
| A-3 | gold (88%) germanium (12%) | 356° C. |
| A-4 | gold (73.3%) indium (26.7%) | 451° C. |
| A-5 | gold (94.0%) silicon (6.0%) | 370° C. |
| B-1 | silver (3.5%) tin (96.5%) | 221° C. |
| B-2 | silver (40%) tin (30%) indium (30%) | 450° C. |
| B-3 | silver (40%) tin (40%) indium (10%) copper (10%) | 458° C. |

TABLE 4-continued

| No. | eutectic alloy (%) by weight | melting temp. |
|---|---|---|
| B-4 | silver (45%) tin (45%) indium (10%) | 472° C. |
| B-5 | silver (5%) tin (95%) | 250° C. |

The reason why the gold is used for the welding member 4, is to improve a visual recognition under the fluoroscopic operation while ameliorating the corrosion-resistance and ductility. The silver is used to adjust the melting temperature of the welding member 4, and the tin is to lower the melting temperature of the welding member 4 to increase the wetting property with the helical spring body 3 and the inner helical spring body 33.

This is true with the indium and copper metals. The germanium metal is used to suppress the intermetallic crystalline from turning coarse, so as to prevent the bonding strength from decreasing to an unacceptable degree.

Reasons why the melting temperature of the welding member 4 in the range 180° C.-495° C. or 180° C.-525° C. are that it becomes difficult to increase the tensile rupture strength of the work-hardened core wire 2 by using the melting heat of the welding member 4 when the melting temperature decreases to less than 180° C. When the melting temperature exceeds 495° C. (525° C. for the Mo-based austenitic stainless steel wire), the austenitic stainless steel wire decreases its tensile rupture strength significantly since when the austenitic stainless steel wire is heated to the temperature of 800° C. which goes beyond 520° C. and 540° C., it becomes to require an energy to precipitate carbonaceous particles and mobilize chromium within the austenitic stainless steel wire (susceptive phenomenon), so as to exceedingly reduce the tensile rupture strength.

This makes it possible to impart the radiotransparent coil 32 and the inner helical spring body 33 with a maximum mechanical strength by suppressing the susceptive phenomenon appeared on the austenitic stainless steel wire.

Melting heat produced by the welding member 4 increases the tensile rupture strength of the metallic wire at the bonding portions, and resultantly increasing the tensile strength at the bonded portions of the radiotransparent coil 32 and the inner helical spring body 33 to improve the fatigue-resistant property against the repetitive bending action.

Upon using the silver-based brazing having the melting temperature of 605° C.-800° C. or the gold-based brazing having the melting temperature of 895° C.-1030° C. as the welding member 4, an amount of melting heat significantly decreases the tensile rupture strength of the metallic wire because the metallic wire is annealed or becomes brittle due to the susceptive phenomenon. This increases the possibility that the helical spring body 3 might be buckled down.

This holds true with the gold-based alloy having around 880° C. as the melting temperature, and made of 74.5%-75.5% gold, 12%-13% silver, iron and lead in less than 0.15% each by weight. Same is true with the silver-based alloy having around 780° C. as the melting temperature, and made of 72% silver and 28% copper by weight.

It is preferable to use the gold metal as the eutectic alloy for the welding member 4 in order to prevent the welding strength from decreasing due to the corrosion, avoiding the welding member 4 from being darkened, and preventing the visual recognition of the welding member 4 from fading away under the fluoroscopic operation.

This is because the medical guide wire 1 is usually dipped in the physiological saline solution before using the medical guide wire 1, and silver sulfide appears on the welding member 4 to darken the welding member 4 within one hour after dipping the guide wire 1 when the silver-based eutectic alloy is used to the welding member 4. With the passage of time, the silver sulfide deeply darkens the welding member 4 to decrease the welding strength due to the corrosion.

Upon connectedly bonding the radiopaque coil 31 and the radiotransparent coil 32 in part by means of the welding member 4, it is possible to favorably improve the wetting relationship between the welding member 4 and radiopaque coil 31 by forming the radiopaque coil 31 with gold, gold-based alloy or gold-plating material.

In order to improve the tensile rupture strength of the radiotransparent coil 32 and the inner helical spring body 33, used is the conduction heat based on the formation generated upon forming the synthetic resin layer 6 on the outer surface of the helical spring body 3.

The synthetic resin layer 6 is formed by means of a dipping method, a heat-wrapping method, an extrusion method or the equivalent. In the dipping method, the helical spring body 3 is heated by dipping it in the melted synthetic resin at 180° C.-450° C. for 1/12-30 minutes including a duration in which the helical spring body 3 is heated by a residual heat. Instead of the helical spring body 3, the radiotransparent coil 32 or the helical spring body 3 may be used after they are bonded to the core wire 2.

In the heat-wrapping method, a heat-shrinkable tube is heated at 180° C.-450° C. for 1/12-30 minutes after the helical spring body 3 is inserted into the heat-shrinkable tube placed in a mould die which has a built-in heater (not shown) to generate a predetermined amount of heat when energized.

In the extrusion method, the helical spring body 3 is inserted into an extrusion head (not shown) which has a built-in heater, the melted synthetic resin is extruded at 180° C.-450° C. for 1/12-30 minutes including the duration in which the helical spring body 3 is heated by the residual heat, so as to form the synthetic resin layer 6 on the outer surface of the helical spring body 3.

In each of the above methods, the helical spring body 3 heat treated by means of the conduction heat (or exterior heat due to the built-in heater) from the synthetic resin layer 6 to the helical spring body 3. The time period heated by the residual heat means the time length required for the helical spring body 3 to descend its temperature from 180° C. to 150° C., a temperature range of which does not contribute to a remarkable improvement of the tensile rupture strength (refer to FIG. 8).

As materials of the synthetic resin layer 6, employed is polyamide 6, 66, 12 or the equivalent, polyamide elastomer, polyurethane, polyurethane elastomer, polypropylene, polypropylene elastomer (including EPR-based additive) or the equivalent.

The polyamide has melting points at 170° C.-260° C. as a melting temperature with $4-8 \times 10^{-4}$ {cal/(cm·sec·° C.)} as a thermal conductivity. The polyurethane has melting points at 180° C.-250° C. as a melting temperature with $3-8 \times 10^{-4}$ {(cal/(cm·sec·° C.)} as the thermal conductivity. The polypropylene has melting points at 170° C.-180° C. and 250° C.-300° C. as a melting temperature with $2.5-4 \times 10^{-4}$ {cal/(cm·sec·° C.)} as the thermal conductivity. Used as the materials of the synthetic resin layer 6 are fluororesins such as PTFE, PFA and FEP which has 253° C.-327° C. as the melting point with $5.7-6.2 \times 10^{-4}$ {cal/(cm·sec·° C.)} as the thermal conductivity.

Upon employing the fluororesin to the synthetic resin layer 6, it is preferable to use the heat-wrapping method in which the synthetic resin is heated at 300° C.-450° C. for 1/12-30 minutes including the duration in which the helical spring body 3 is heated by the residual heat.

A lower duration time limit of the heat treatment in low temperature is determined to be 1/12 minutes because the thinned or very thinned metallic wire has a low calorific capacity and very susceptible to the thermal influence.

An upper duration time limit of the heat treatment in low temperature is determined to be 30 minutes because the helical spring body 3 is heat treated within the temperature range in which the tensile rupture strength is improved.

The helical spring body 3 (radiotransparent coil 32) is heat treated in low temperature through the conduction heat generated upon forming the synthetic resin layer 6 on the outer surface of the helical spring body 3. The metallic wire employed to the transparent coil 32 and the inner helical spring body 33 have 15-15.6 $(W \cdot m^{-1} \cdot K^{-1})$ as a heat conductivity at normal temperature.

Since the synthetic resin layer 6 has $2.5-4.0 \times 10^{-4}$ {cal/(cm·sec·° C.)} as the lowest thermal conductivity, it is possible to convey the conduction heat from the melted synthetic resin having $2.5 \times 10^{-4}$ {cal/(cm·sec·° C.)} or more to the metallic wire of the radiotransparent coil 32 having 15 $(W \cdot m^{-1} \cdot K^{-1})$ or more as the heat conductivity at normal temperature with the whole cross sectional reduction ratio as 90%-99.5%.

After the metallic wire is highly drawn and wound to form the radiotransparent coil 32, the radiotransparent coil 32 is heat treated at low temperature, a range of which makes the tensile rupture strength rapidly increase with the use of melting heat generated from the melted synthetic resin upon applying the melted synthetic resin to the outer surface of the radiotransparent coil 32.

With the use of conduction heat conveyed to the helical spring body when the synthetic resin layer is melted, it is possible to fully disperse a concentrated stress locally occurred on the helical spring body 3 due to the winding procedure when forming the metallic wire into the helical spring body 3, thereby homogenizing an entire texture of the helical spring body 3 so as to improve the fatigue-resistant property of the helical spring body 3 against the repetitive bending action.

Further, the helical spring body 3 (radiotransparent coil 32) is heat treated in low temperature by the conduction heat based on the melting heat when the helical spring body 3 and the core wire 2 are connectedly bonded by means of the welding member 4, while at the same time, heat treated based on the conduction heat generated upon forming the synthetic resin layer 6 on the helical spring body 3.

As the materials of the welding member, the gold metal has 313-319 $(W \cdot m^{-1} \cdot K^{-1})$, the silver metal has 422-428 $(W \cdot m^{-1} \cdot K^{-1})$ and the tin metal has 63-68 $(W \cdot m^{-1} \cdot K^{-1})$ as the heat conductivity at normal temperature.

Since the tin metal has the lowest heat conductivity among the above metals, it is possible to convey the conduction heat from the eutectic alloy of the welding member 4 and the conduction heat of the synthetic resin layer 6 to the metallic wire of the radiotransparent coil 32.

By way of illustration, the eutectic alloy of the welding member 4 has 63 $(W \cdot m^{-1} \cdot K^{-1})$ or more, and the synthetic resin layer 6 has $2.5 \times 10^{-4}$ {cal/(cm·sec·° C.)} or more, and the metallic wire of the radiotransparent coil 32 has 15 $(W \cdot m^{-1} \cdot K^{-1})$ or more as the heat conductivity at normal temperature with the whole cross sectional reduction ratio as 90%-99.5%.

Such is the structure that after forming the metallic wire into the radiotransparent coil 32, the radiotransparent coil 32 is heat treated at low temperature, a range of which makes the tensile rupture strength rapidly increase with the use of melting heat generated from the melted synthetic resin when applying the synthetic resin layer to the outer surface of the radiotransparent coil 32. At the same time, the radiotransparent coil 32 is heat treated at low temperature, a range of which makes the tensile rupture strength rapidly increase with the use of melting heat generated when the welding member 4 is melted.

With the use of conduction heat concurrently conveyed to the helical spring body 3 when the synthetic resin layer 6 and the welding member 4 are melted, it is possible to fully disperse a concentrated stress locally occurred on the helical spring body 3 when forming the metallic wire into the helical spring body 3, thereby homogenizing the entire texture of the helical spring body 3 so as to additionally improve the fatigue-resistant property of the helical spring body 3 against the repetitive bending action.

Reverting to FIG. 1 which shows that the intermediate front weld portion 41 is a bonded portion placed between the radiotransparent coil 32 and the radiopaque coil 31, the helical spring coil 3 is subjected to a third conduction heat from the radiopaque coil 31 to the radiotransparent coil 32.

This means that the helical spring coil 3 is heat treated in low temperature with a first conduction heat generated by the welding member 4 melted when partly bonding the radiopaque coil 31 and the radiotransparent coil 32 to the core wire 2, and a second conduction heat generated from the melted synthetic resin when forming the synthetic resin layer 6.

As the metallic materials of the radiopaque coil 31, the gold metal or gold-plated metal has 313-319 $(W \cdot m^{-1} \cdot K^{-1})$ as the heat conductivity at normal temperature. The tungsten (wolfram) metal and platinum metal have 163-177 and 72-73 $(W \cdot m^{-1} \cdot K^{-1})$ in turn as the heat conductivity at normal temperature.

For this reason, it is possible to heat treat the helical spring body 3 in low temperature through the first, second and third conduction heat conveyed from the radiopaque coil 31 to the metallic wire (austenitic stainless steel wire) of the radiotransparent coil 32 having 15 $(W \cdot m^{-1} \cdot K^{-1})$ or more as the heat conductivity at normal temperature with the whole cross sectional reduction ratio as 90%-99.5%.

The first conduction heat comes from the eutectic alloy of the welding member 4 having 63 $(W \cdot m^{-1} \cdot K^{-1})$ or more as the heat conductivity at normal temperature.

The second conduction heat comes from the synthetic resin layer 6 having $2.5 \times 10^{-4}$ {cal/(cm·sec·° C.)} or more as the thermal conductivity at normal temperature.

The third conduction heat comes from the radiopaque coil 31 having the heat conductivity four times greater than that of the radiotransparent coil 32 at normal temperature.

Reason why the radiopaque coil 31 has the heat conductivity four times greater than that of the radiotransparent coil 32 is to show an example when the radiopaque coil 31 contains the platinum metal or platinum-based alloy as described in detail hereinafter.

Such is the structure that after forming the metallic wire into the radiopaque coil 31 and the radiotransparent coil 32, the welding member 4 has the melting temperature, a range of which rapidly increases the tensile rupture strength of the metallic wire. The synthetic resin layer 6 has the melting temperature, a range of which rapidly increases the tensile rupture strength of the metallic wire when applying the synthetic resin layer 6 to the outer surface of the helical spring body 3. The welding member 4 and the synthetic resin layer 6 have the melting heat as the first and second conduction heat in turn when they reach the melting temperature.

Further, the melting heat is generated as the third conduction heat at the bonded portion in which the radiopaque coil 31 and the radiotransparent coil 32 are bonded by means of the welding member 4, and when the melted synthetic resin is applied to the outer surface of the helical spring body 3. The melting heat has three types of thermal transference as the first, second and third conduction heat and is concurrently conveyed from the radiopaque coil 31 to the radiotransparent coil 32 to heat treat the helical spring body 3 in low temperature.

This makes it possible to fully disperse a concentrated stress locally occurred when forming the metallic wire into the helical spring body 3, thereby entirely homogenizing the bonded portion and the helical spring body 3 so as to all the more improve the fatigue-resistant property of the helical spring body 3 against the repetitive bending action.

Due to the heat treatment in low temperature at the time of forming the synthetic resin 6 and melting the welding member 4, it is possible to fully disperse the concentrated stress and the residual stress each locally occurred on the radiotransparent coil 32 when winding the metallic wire into the helical spring body 3, while at the same time, improving the tensile rupture strength of the metallic wire. This is because the melted synthetic resin and the welding member 4 have the melting temperature, the range of which makes the tensile rupture strength increase (refer to FIG. 8). Considering a synergistic effect the second conduction heat combined with the first and third conduction heat, it is possible to further improve the tensile rupture strength of the metallic wire of the helical spring body 3.

Since the synthetic resin layer 6 tightly seals the radiotransparent coil 32 while conveying the conduction heat from the melted synthetic resin and welding member 4 to the radiotransparent coil 32, the residual heat lingers within a pneumatic space between the helical spring body 3 and the distal end portion 21 of the core wire 2, the metallic wire of the radiotransparent coil 32 is very susceptible to the thermal influence. This is all the more true when considering the metallic wire of the radiotransparent coil 32 is thin or very thin (0.050 mm-0.095 mm in diameter).

Due to the formation heat generated upon forming the synthetic resin layer 6, it is possible to heat treat the entirety of the helical spring body 3 in low temperature, it is possible to fully disperse the concentrated stress and the residual stress each locally occurred on the radiotransparent coil 32 when winding the metallic wire into the helical spring body 3, thereby bending the helical spring body 3 in a smooth and uniform radius of curvature.

In order to effectively improve the tensile rupture strength of the metallic wire of the radiotransparent coil 32, it is possible to efficiently use the first conduction heat from the radiopaque coil 31 to heat treat the radiotransparent coil 32 in low temperature. For this purpose, it is preferable to determine the heat conductivity of the radiopaque coil 31 to be four times greater than that of the radiotransparent coil 32 at normal temperature.

When the radiopaque coil 31 is made of the platinum metal or platinum-based alloy, the heat conductivity of the radiopaque coil 31 is to be approximately 4.3 times greater than that of the radiotransparent coil 32. When the radiopaque coil 31 is made of the tungsten metal or tungsten-based alloy, the heat conductivity of the radiopaque coil 31 is to be approximately 7.3 times greater than that of the radiotransparent coil 32. When the radiopaque coil 31 is made of the gold metal or gold-based alloy, the heat conductivity of the radiopaque coil 31 is to be approximately 15.7 times greater than that of the radiotransparent coil 32.

For the purpose of implementing the heat treatment in low temperature, it is preferable to positively utilize the melting heat of the welding member 4 and the melting heat produced upon forming the synthetic resin layer 6 on the outer surface of the helical spring body 3 because of their greater calorific capacity.

Since the gold metal and silver metal have 299 and 407 ($W \cdot m^{-1} \cdot K^{-1}$) in turn as the heat conductivity at 300° C., the heat conductivity of the gold metal and silver metal is approximately 18.1 (299/16.5) times and 24.7 (407/16.5) times greater than that of the radiotransparent coil 32. By employing the gold-based or silver-based alloy to the welding member 4, it is possible to efficiently implement the thermal conveyance toward the radiotransparent coil 32 so as favorably heat treat the radiotransparent coil 32 in low temperature.

The radiopaque coil 31 includes a coil, an outer surface of which is coated with a radiopaque thin layer by means of a plating and sputtering procedure.

Figure 11:
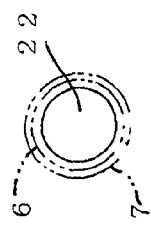
FIG. 11 is a right side elevational view of the medical guide wire.
Figure 10:
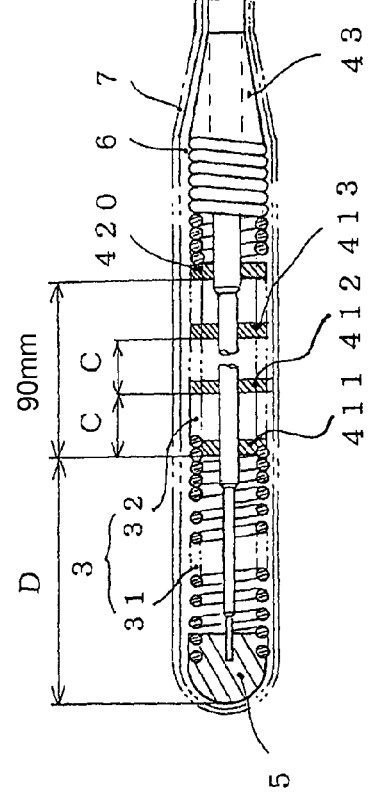
FIG. 10 is a longitudinal cross sectional view of a medical guide wire according to a second embodiment of the invention.
Figure 12:
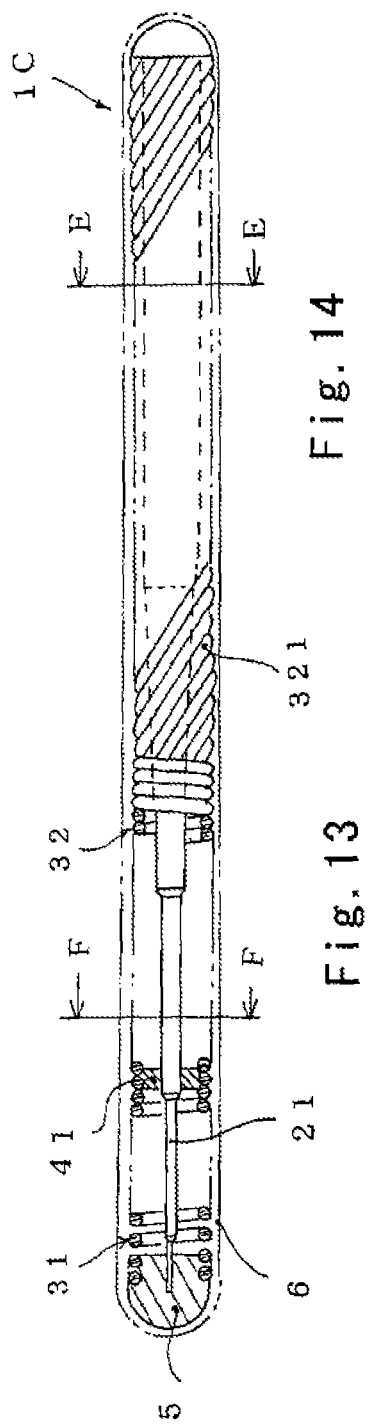
FIG. 12 is a longitudinal cross sectional view of a medical guide wire according to a third embodiment of the invention.

FIGS. 10 and 11 show a second embodiment of the invention in which a medical guide wire 1B has the radiotransparent coil 32 formed by the metallic wires 1a-1f.

Between an outer surface of the core wire 2 and an inner surface of the helical spring body 3, there are provided a plurality of intermediate front weld portions 411-420 arranged lengthwise at regular intervals (C: e.g., 10 mm) along the core wire 2 beyond a portion proximally distanced by a predetermined length (D: e.g., 50 mm) from a distal extremity of the head plug 5. Although the number of the intermediate front weld portions 411-420 is counted as ten to extend by 90 mm along the lengthwise direction, the intermediate front weld portions 414-419 are omitted for the sake of convenience.

By forming the intermediate front weld portions 411-420 with the use of the welding member 4, it is possible to heat treat the radiotransparent coil 32 in low temperature without using the furnace, so as to improve the tensile rupture strength of the bonded portions of the intermediate front weld portions 411-420 against the helical spring body 3.

This makes it possible to improve the fatigue-resistant property at the bonded portions of the helical spring body 3 against the repetitive bending action.

This also enables the user to improve the tensile rupture strength of any part of the helical spring body 3, especially improving the bonded portions which are likely subjected to an excessive amount of bending stress when the medical guide wire 1B is bent.

By applying the welding member 4 to the radiopaque material represented by e.g., A-1 in Table 4, it is possible to make use of the intermediate front weld portions 411-420 as a scale measurer which enables the user to determine a dimensional length of a stenotic area within a vasculature of a somatic cavity. It is to be noted that the intermediate front weld portions 411-420 may be arranged regularly in arithmetic or geometric progression.

As mentioned previously in the first embodiment of the invention, it is preferable to use the gold metal as the eutectic alloy for the welding member 4 in order to prevent the welding strength from decreasing due to the corrosion, avoiding the intermediate front weld portions 411-420 from being darkened, and preventing their visual recognition from fading away under the fluoroscopic operation since the medical guide wire 1B is usually dipped in the physiological saline solution before using the medical guide wire 1B.

Figure 14:
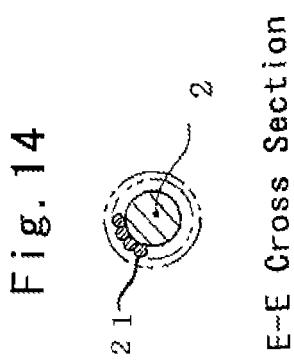
FIG. 14 is a latitudinal cross sectional view taken along the line E-E of FIG. 12.
Figure 13:
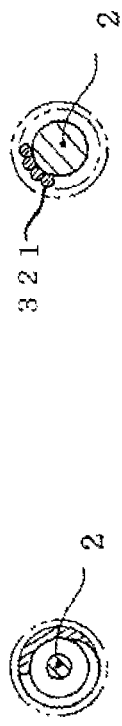
FIG. 13 is a latitudinal cross sectional view taken along the line F-F of FIG. 12.

FIGS. 13 through 14 show a third embodiment of the invention in which a medical guide wire 1C has a coil body 321 connected to the radiotransparent coil 32 provided around the core wire 2 approximately by the length of 900 mm-2400 mm. The coil body 321 is formed by stranding a plurality of thin wires, the material of which is the same as that of the radiotransparent coil 32.

Figure 15:
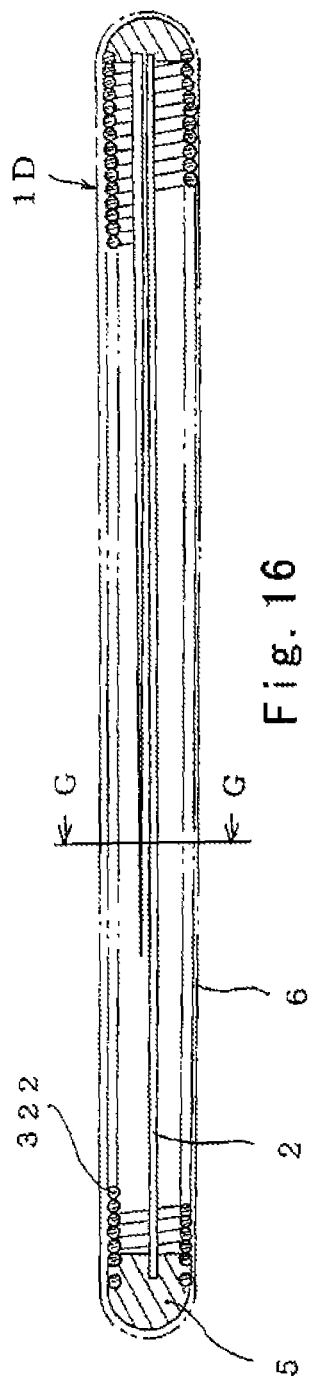
FIG. 15 is a longitudinal cross sectional view of a medical guide wire according to a fourth embodiment of the invention.
Figure 16:
FIG. 16 is a latitudinal cross sectional view taken along the line G-G of FIG. 15.

FIGS. 15 and 16 show a fourth embodiment of the invention in which a medical guide wire 1D has a coil body 322 placed around an entire length of the core wire 2. To the head plug 5 or a distal end of the core wire 2, the coil body 322 is bonded by means of the welding member 4. The coil body 322 has the same material as that of the radiotransparent coil 32.

FIGS. 17 and 18 show a fifth embodiment of the invention in which a medical guide wire 1E has the radiopaque coil 31 and a radiotransparent coil 323, each length of which is limited as a first and second coil unit around the distal end portion of the core wire 2. Both ends of the radiopaque coil 31 and both ends of the radiotransparent coil 323 are bonded to the core wire 2 by means of the welding member 4. An outer surface of the radiopaque coil 31 and an outer surface of the radiotransparent coil 323 are coated with the synthetic resin layer 6. The radiotransparent coil 323 has the same material as that of the radiotransparent coil 32. It is to be noted that a plurality of the radiopaque coils 31 and a plurality of the radiotransparent coils 323 may be arranged lengthwise at regular intervals.

By applying the metallic wires 1a-1g to the radiotransparent coils 321-323, it is possible to improve the tensile rupture strength of the bonded portions of the radiotransparent coils due to the melting heat of the welding member 4, so as to improve the fatigue-resistant property against the repetitive bending action. Due to the formation heat generated upon forming the synthetic resin layer 6, it is possible to improve the tensile rupture strength of the radiotransparent coils, and fully disperse the concentrated stress and the residual stress so as to bend the radiotransparent coils in a smooth and uniform radius of curvature.

Figure 19:
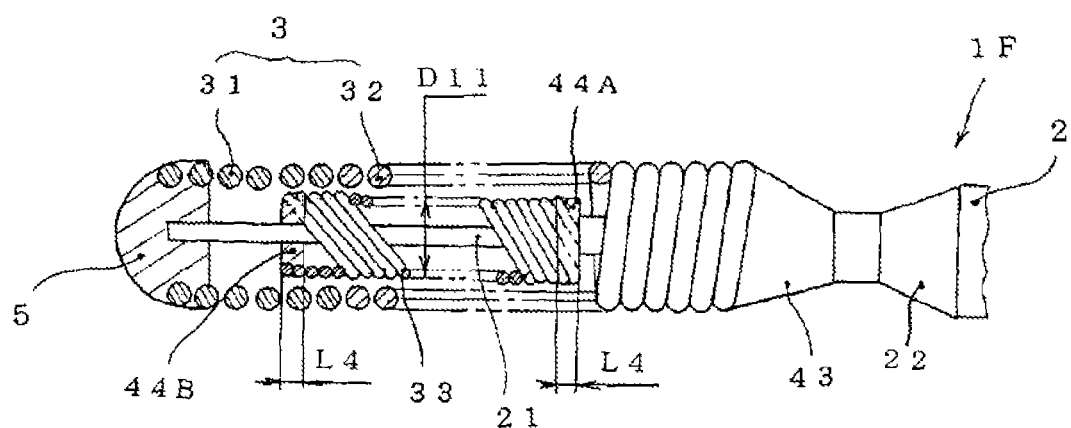
FIG. 19 is a longitudinal cross sectional view of a medical guide wire according to a sixth embodiment of the invention.
Figure 20:
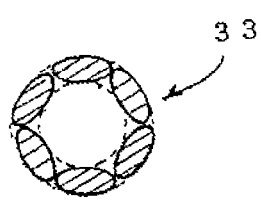
FIG. 20 is a latitudinal cross sectional view of the medical guide wire.

FIGS. 19 and 20 show a sixth embodiment of the invention in which a medical guide wire 1F has the inner helical spring body 33 around the distal end portion 21 of the core wire 2. The inner helical spring body 33 is reduced in length more than the helical spring body 3, and concentrically placed inside the helical spring body 3 so as to form a multi-layered construction as shown in FIG. 19.

The inner helical spring body 33 has the metallic wire employed to that of the radiotransparent coil 32. By using the melting heat of the welding member 4, it is possible to improve the tensile rupture strength of the helical spring body 3 and the inner helical spring body 33 so as to ameliorate their fatigue-resistant property against the repetitive bending action.

Due to the multi-layered construction, it is possible to quickly reinstate the medical guide wire 1F to the original linear-configuration after bending it into a U-shaped configuration, and remarkably ameliorating the torque transmissibility conveyed from the proximal end portion to the distal end portion of the medical guide wire 1F.

A proximal weld portion 44A between the core wire 2 and a proximal end of the inner helical spring body 33 forms a doughnut- or torus-shaped ring body, a thickness L4 of which ranges from 0.1 mm to 1.5 mm.

A distal weld portion 44B between the core wire 2 and a distal end of the inner helical spring body 33 forms a doughnut- or torus-shaped ring body, a thickness L4 of which ranges from 0.1 mm to 1.5 mm. It is to be noted that the doughnut- or torus-shaped weld portions between the core wire 2 and a middle section of the inner helical spring body 33 are as represented by numerals 41 and 42 in FIG. 1.

In FIGS. 19, 20, the synthetic resin layer 6 and the hydrophilic film 7 are omitted for the sake of convenience. The same is true with FIGS. 21-23 described in detail hereinafter.

More specific, the inner helical spring body 33 is formed by stranding 3-12 pieces of metallic wires 1g (e.g., 0.030 mm in diameter) around an elongate core (not shown) to provide a rope-stranded configuration in which side wires are stranded around the elongate core. By withdrawing the elongate core from the side wires, the side wires remains to form a wire-stranded hollow tube, an outer diameter of which measures e.g., 0.185 mm (0.050 mm-0.210 mm). Six pieces of metallic wires are used to form the inner helical spring body 33 as shown in FIG. 20. It is to be noted that the metallic wires 1g may have a diameter ranging from 0.010 mm to 0.040 mm.

With the inner helical spring body 33 formed by stranding a plurality of metallic wires, it is possible to prevent the clearance from spreading between neighboring helices of the helical spring body 33. This makes it possible to attain a uniform radius of curvature at the bent portion of the medical guide wire 1F, thereby enhancing the torque-transmissibility conveyed from the proximal end portion 22 through the distal end portion 21 of the core wire 2 to the head plug 5, while at the same time, ameliorating a restitution capability to reinstate the original linear-configuration after the medical guide wire 1F is curvedly bent.

In the same manner as mentioned at the radiotransparent coil 32, the metallic wire employed to the inner helical spring body 33 is the austenitic stainless steel wire treated with the solid-solution procedure, and may be subjected to at least three sets with the combination of the wire-drawing procedure and the heat treatment at low temperature as a single one set before finally drawn.

Alternatively, as the same manner of the metallic wires 1a, 1c, the metallic wire employed to the inner helical spring body 33 is the austenitic stainless steel wire treated with the solid-solution procedure may be highly drawn without primarily heat treated in low temperature, and heat treated in low temperature after formed into the inner helical spring body.

It is preferable that the metallic wire of the inner helical spring body 33 has 90%-99.5% as the whole cross sectional reduction ratio with the tensile rupture strength as 210 kgf/mm$^2$-450 kgf/mm$^2$, and more preferable that the metallic wire of the inner helical spring body 33 has 90%-99% as the whole cross sectional reduction ratio with the tensile rupture strength as 210 kgf/mm$^2$-400 kgf/mm$^2$.

In order to provide the metallic wire (0.01 mm-00.040 mm in diameter) with a high tensile rupture strength, it is preferable that the metallic wire of the inner helical spring body 33 has 94% or more as the whole cross sectional reduction ratio, and more preferable that the metallic wire has 97%-99.5% as the whole cross sectional reduction ratio, and most preferable that the metallic wire has 97%-99% with the tensile rupture strength as 400 kgf/mm$^2$ or less.

The reason why the whole cross sectional reduction ratio is predetermined above is the same as mentioned in the radiotransparent coil 32.

Figure 21:
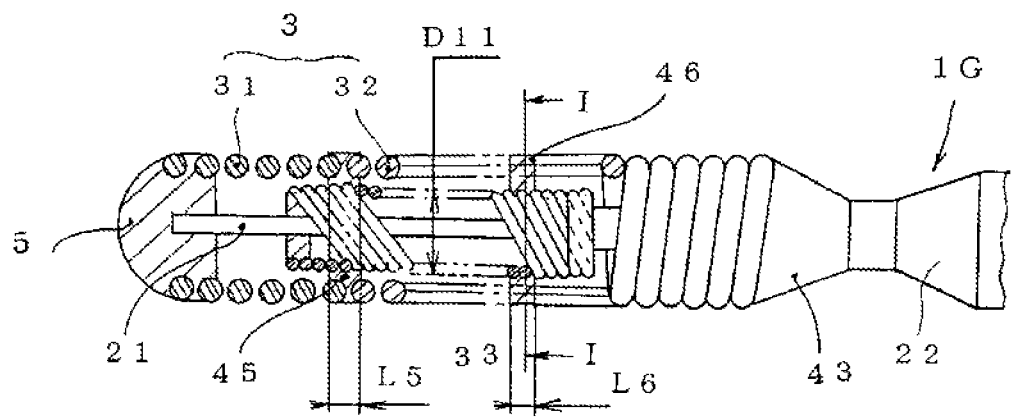
FIG. 21 is a longitudinal cross sectional view of a medical guide wire according to a seventh embodiment of the invention.
Figure 22:
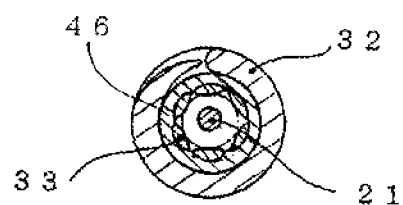
FIG. 22 is a latitudinal cross sectional view taken along the line I-I of FIG. 21.

FIGS. 21 and 22 show a seventh embodiment of the invention in which a medical guide wire 1G has an intermediate front weld portion 45 configured into a doughnut- or torus-shaped ring body at a portion in which the radiopaque coil 31, the inner helical spring body 33 and the distal end portion 21 of the core wire 2 are integrally bonded by means of the welding member 4.

The medical guide wire 1G further has an intermediate rear weld portion 46 configured into a doughnut- or torus-shaped ring body at a portion in which the radiotransparent coil 32, the inner helical spring body 33 and the distal end portion 21 of the core wire 2 are integrally bonded by means of the welding member 4. The intermediate front weld portion 45 and the intermediate rear weld portion 46 have 0.3 mm-5 mm in thickness as designated by L5 and L6 in FIGS. 21 and 22.

Such is the structure that the core wire 2 enables the proximal end 22 to send its rotational transmission force to the distal end side of both the helical spring body 3 and the inner helical spring body 33 so as to remarkably ameliorate the torque transmissibility toward the distal end side of both the helical spring body 3 and the inner helical spring body 33. This is because the torsional force (torsional moment M) of both the helical spring body 3 and the inner helical spring body 33 is in inverse proportion to an average diameter Do and number N of winding turns of the both the helical spring body 3 and the inner helical spring body 33 (M∝1/Do×1/N).

By way of illustration, when the single one intermediate front weld portion 45 is placed in the middle of the helical spring body 3, the number N of the winding turns of the helical spring body 3 is counted as ½ to increase the torsional moment M by two fold in its magnitude.

Under the presence of the intermediate front weld portion 45 and the intermediate rear weld portion 46, the number N of the winding turns of the helical spring body 3 further decreases to increase the torsional moment M by the amount in which the number N of the winding turns diminishes, thereby contributing to strengthening the rotational transmission toward the distal end of the helical spring body 3. The same is true with the inner helical spring body 33. By means of the intermediate front weld portion 45 and the intermediate rear weld portion 46, it is possible to rotationally turn the helical spring body 3 and the inner helical spring body 33 together. By means of the melting heat produced by the welding member 4, it is possible to improve the tensile rupture strength at the metallic wire by which the helical spring body 3 and the inner helical spring body 33 are made.

Figure 23:
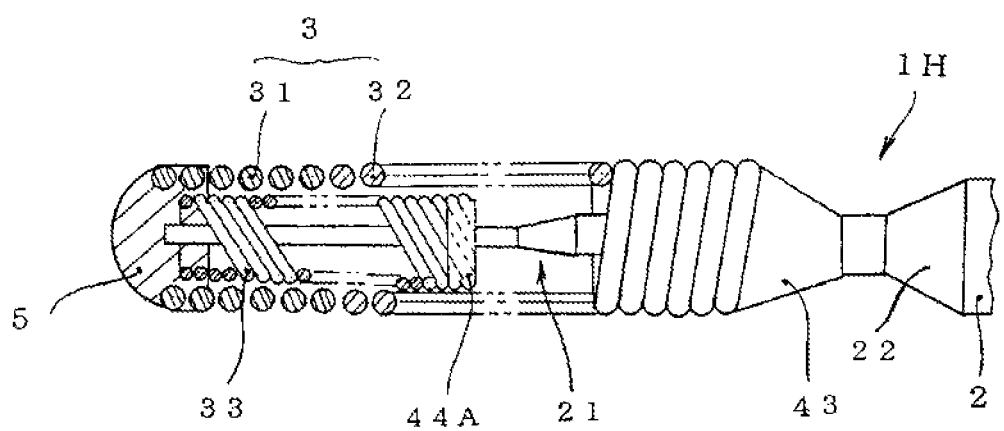
FIG. 23 is a longitudinal cross sectional view of a medical guide wire according to an eighth embodiment of the invention.

FIG. 23 shows an eighth embodiment of the invention in which a medical guide wire 1H has the inner helical spring body 33, a distal end of which is integrally bonded in part to the head plug 5.

With the melting heat produced by the welding member 4, it is possible 10 improve the tensile rupture strength of the metallic wire of the inner helical spring body 33, while at the same time, ameliorating the rotational transmission toward the distal end of the inner helical spring body 33, further increasing the restoring force of the inner helical spring body 33 after curvedly bent into the U-shaped configuration, and resultantly improving the fatigue-resistant property at the bonded portion (between the distal end portion 21 and the plug head 5) against the repetitive bending action. It is to be noted that the intermediate front weld portion 45 and the intermediate rear weld portion 46 may be placed respectively at the middle of the inner helical spring body 33 as observed in the seventh embodiment of the invention.

FIGS. 24 and 25 show an assembly suited for therapeutically treating the stenotic area of the vasculature at the lower limb with the use of the medical guide wire 1 (1A-1H).

In FIGS. 24 and 25 which depict how to advance the medical guide wire into the stenotic area of the vasculature, so as to smoothly advance the medical guide wire 1C into the obstructed area 9C of the tibial artery 9B as shown in FIG. 24, the medical guide wire 1C is advanced through the femoral artery 9A before reaching the bifurcated portion 9D with the distal end portion U curvedly bent when the distal end portion U of the medical guide wire 1C is bent into the U-shaped configuration as shown in FIG. 25. After reaching the bifurcated portion 9D, the medical guide wire 1C is pulled to be set straight (S1) before finally advanced to the obstructed area 9C as shown by S2 in FIG. 25.

Due to the metallic wire of the radiotransparent coil 32 and the inner helical spring body 33, the tensile rupture strength of which is additionally improved by means of the welding heat produced by the welding member 4, the medical guide wire restores the distal end portion U to the original straight configuration from the U-shaped configuration without retaining the bending tendency at the bifurcated portion 9D.

Especially, the medical guide wires 1F-1H effectively restore the distal end portion 21 of the core wire 2 to the original straight configuration from the U-shaped configuration because the medical guide wires 1F-1H have the inner helical spring body 33 made of the multitude of the stranded metallic wires, the tensile rupture strength of which is highly improved.

In this instance, the helical spring body 3 and the head plug 5 have the outer diameter (D1, D2, D6) as approximately 0.457 mm (0.018 inches). When the medical guide wire 1 is combined with a guiding catheter 11 and a microcatheter 10, the latter of which has a wire-stranded hollow structure made of the multitude of metallic wires, an outer surface of the microcatheter 10 forms concave-convex configuration which supports a reactional force of the medical guide wire 1 to provide the medical guide wire 1 with a forward propelling force. By determining an inner diameter of the guiding catheter 11 to be 1.91 mm-2.67 mm, it is possible to render the medical guide wire 1 suited for the guiding catheter 11 as the assembly of the medical tool.

With the use of the medical guide wire 1 made of the helical spring bodies 3, 33, it is possible to diametrically reduce the medical guide wire 1 suited for therapeutically treating the cardiovascular disease because of the helical spring body 3, an outer diameter of which is reduced to such a degree as, for example, 0.355 mm-0.228 mm (0.014 inches-0.009 inches).

Upon building the assembly, the medical guide wire 1 is inserted into the microcatheter 10, and the microcatheter 10 is inserted into the guiding catheter 11 with the medical guide wire 1 inserted into the microcatheter 10.

In combination with the reduced diameter of the medical guide wire 1, it is possible to reduce the inner diameter of the guiding catheter 11 to 6F (1.91 mm-2.00 mm) from 7 F-8 F (2.3 mm-2.7 mm), while at the same time, reducing the inner diameter of the microcatheter 10 to 0.28 mm-0.90 mm.

The vasculature at the lower limb is two or three times thicker than the cardiovascular tract, and the stenotic area is three times longer than the obstructed area of the cardiovascular tract. It is necessary for the medical guide wire 1 to have its entire diameter (D1, D2, D6, D7 in FIG. 1) to be 0.457 mm (0.018 inches) in order to gain the reactional force which forcibly advances the medical guide wire 1 through the vasculature at the lower limb.

As for the microcatheter 10 which is subjected to the reactional force to support the reactional force as the forward propelling force against the medical guide wire 1, it may be a multi-layered structure in which inner layer (PTFE) and an outer polyimide layer are provided. In this situation, a braided metallic wire may be inserted into the multi-layered structure.

The microcatheter 10 may be made from a wire-stranded hollow tube having a metallic or synthetic distal cylinder tip 10B, an outer surface of which is distally tapered off. The distal tip cylinder 10B may have a drilling function which makes it possible to perforate the obstructed area of the vasculature. The wire-stranded hollow tube is formed by a plurality of metallic wires circular in cross section.

The microcatheter 10 may be made from a wire-stranded flexible tube having a cone-shaped distal tip formed with the synthetic resin so as to readily insert the distal tip into the obstructed area curved in a meandering fashion.

It is unavoidable for the user to meet the thin arteries curved in the meandering fashion for the cardiovascular treatment, and confronting the stenotic area (or completely obstructed area) three times or more longer than the obstructed area of the cardiovascular tract for treating the vasculature at the lower limb. In order to perforate the stenotic area, it is preferable to use the wire-stranded hollow tube, the outer surface of which forms the concave-convex configuration.

Figure 26:
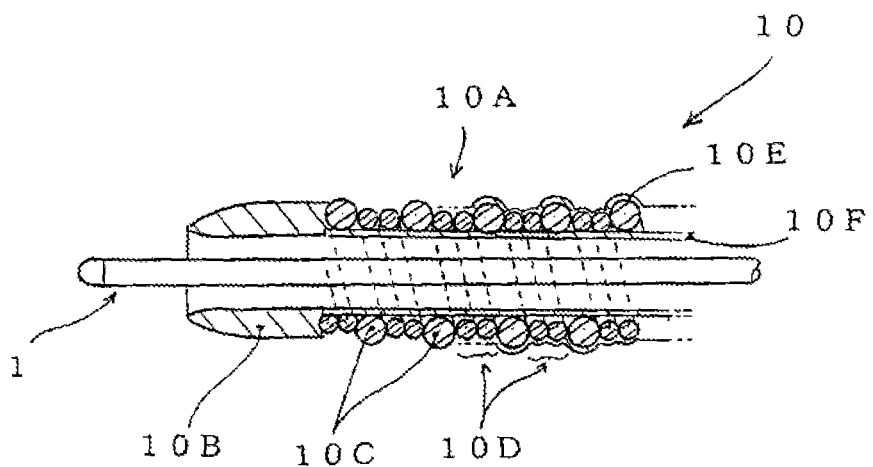
FIG. 26 is a longitudinal cross sectional view of a medical guide wire according to a ninth embodiment of the invention.

In FIG. 26, a wire-stranded hollow tube 10A is shown as a ninth embodiment of the invention in which the wire-stranded hollow tube 10A is made by alternately winding or twisting thick wires 10C (0.11 mm-0.18 mm in diameter) and thin wires 10D (0.06 mm-0.10 mm in diameter). Number of the thick wires 10C ranges from one to two, and number of the thin wires 10D ranges from two to eight.

Alternatively, a paired liner may be formed by combining one thick wire with the thin wires, the number of which ranges from two to eight. Two or more paired liners are wound or twisted with the metallic wires abutted each other to form a wire-stranded hollow tube, an outer surface of which defines the concave-convex configuration.

Upon inserting the medical guide wire 1 into the blood vessel, the wire-stranded hollow tube makes its concave-convex surface contact with the vascular wall of the blood vessel to prevent the concave-convex surface from slipping along the vascular wall. This makes it possible for the wire-stranded hollow tube to support the reactional force which works against the wire-stranded hollow tube against the medical guide wire 1.

The wire-stranded hollow tube preferentially makes the thick wires 10C contact with the vascular wall, and moves predominantly by a greater pitch of the thick wires 10C so as to move back and forward in a longer distance when the medical guide wire 1 is rotationally operated as the assembly.

An inner surface of the wire-stranded hollow tube 10A has a first synthetic thin tube 10F, and an outer surface of the wire-stranded hollow tube 10A has a second synthetic thin tube 10E. The synthetic thin tubes 10F, 10E are flexible enough to permit a concave-convex surface to appear on a distal end portion or an entire length of the outer surface of the second synthetic thin tube 10E.

It is to be noted that the concave-convex surface may appear on the second synthetic thin tube 10E at least within a distance of 300 mm from the distal end of the wire-stranded hollow tube 10A when the second synthetic thin tube 10E is subjected to deformation due to an exterior pressure or a pushing force from the vascular wall upon inserting the wire-stranded hollow tube 10A into the blood vessel.

It is preferable to apply the same metallic wire as employed to the inner helical spring body 33 and the radiotransparent coil 32 upon arranging the thick wires 10C and thin wires 10D.

Upon therapeutically treating the stenotic area grown at both sides of the bifurcated portion, an assembly is used which combines the medical catheter 1 with the guiding catheter 11 and a balloon catheter (not shown). Immediately before reaching the stenotic area of the bifurcated portion, the balloon catheter inflates a balloon portion to advance it into the vascular wall. With the reactional force supported by the guiding catheter 11, it is possible to impart the medical guide wire 1 with the forward propelling force so as to readily handling the kissing operation.

Upon implementing the kissing operation, two paired units are inserted into the guiding catheter 11 with a combination of the medical guide wire 1 and the balloon catheter as a paired unit. The balloon catheters expand the respective balloon portions concurrently to dilate the vascular wall of the stenotic area at both sides behind the bifurcated portion.

As the assembly of the balloon catheter and the guiding catheter 11 combined with the medical guide wire 1, an outer diameter of the medical guide wire 1 measures 0.228 mm-0.254 mm (0.009 inches-0.018 inches) which is inserted into the balloon catheter, an inner diameter of which measures 0.28 mm-0.90 mm. Two pairs of the medical guide wire and the balloon catheter are inserted into the guiding catheter 11, an inner diameter of which measures 1.91 mm-2.67 mm.

It is to be noted that the helical spring body 3 may be comprised of a diameter-reduced front coil and a diameter-enlarged rear coil, each of which has an equi-diametrical dimension along the lengthwise direction of the medical guide wire 1. The helical spring body 3 may increase its diametrical dimension progressively from the distal end to the proximal end of the medical guide wire 1 so as to form a tapered tube structure.

While several illustrative embodiments of the invention have been shown and described, variations and alternate embodiments will occur to those skilled in the art. Such variations and alternate embodiments are contemplated, and can be made without departing from the spirit and scope of the invention as defined in the appended claims.

What is claimed is:

1. A medical guide wire which has a core wire formed by a flexible elongate member, the core wire inserted to a helical spring body made of a radiotransparent coil, the core wire and the radiotransparent coil in part secured by a welding member, comprising:

the radiotransparent coil being made by a metallic wire element wound in a spiral fashion;

the metallic wire element made of an austenitic stainless steel wire treated with a solid-solution procedure, and drawn by a wire-drawing procedure with a whole cross sectional reduction ratio as 90%-99.5%, the solid-solution procedure meaning to form a uniform solid phase by evenly melting two or more metallic components;

the welding member being made of a eutectic alloy having a melting temperature of 180° C.-495° C. including a eutectic alloy having a melting temperature of 180° C.-525° C. when the metallic wire element of the radiotransparent coil contains molybdenum as a component element of the austenitic stainless steel wire;

the core wire and the radiotransparent coil in part secured by the welding member, wherein melting heat of the welding member increases a tensile rupture strength of the metallic wire element of the radiotransparent coil; and the whole cross sectional reduction ratio R being expressed by R=(S1-S2)/S1, where S1 is a cross sectional area regarding an original diameter of the metallic wire element treated with the solid-solution procedure before the metallic wire element is drawn, and S2 is a resultant cross sectional area regarding a finished diameter of the metallic wire element treated with the solid-solution procedure after the metallic wire element is drawn.

2. The medical guide wire according to claim 1, wherein a distal end side of the helical spring body has a radiopaque coil and a proximal end side of the helical spring body has a radiotransparent coil with a distal end portion of the core wire inserted into the helical spring body;

a metallic wire element of the radiotransparent coil being made of an austenitic stainless steel wire treated with a solid-solution procedure, and drawn until the whole cross sectional reduction ratio comes to 90%-99.5% with a predetermined tensile rupture strength, melting heat of the welding member working to increase a tensile rupture strength of the metallic wire element of the radiotransparent coil; and a relationship between X and Y being defined as follows:

$$Y \geq 1.555X + 70$$

where X (%) is the whole cross sectional reduction ratio, and Y (kgf/mm$^2$) is the tensile rupture strength represented by Rp=P1/Sp, where P1 is a magnitude of a tensile force applied, and Sp is a cross sectional area of the metallic wire element when the metallic wire element surrenders to disconnection.

3. The medical guide wire according to claim 1, wherein the metallic wire element of the radiotransparent coil being made of an austenitic stainless steel wire treated with a solid-solution procedure, and drawn by a wire-drawing procedure to be heat treated thereafter at low temperature of 300° C.-495° C. or heat treated at low temperature of 300° C.-525° C. when the metallic wire element of the radiotransparent coil contains molybdenum as a component element of the austenitic stainless steel wire;

the metallic wire element being finally drawn after implementing at least one set or more with a combination of the wire-drawing procedure and the heat treatment at low temperature as a single one set;

the metallic wire element having the whole cross sectional reduction ratio as 90%-99.5% after finally drawn, melting heat of the welding member increasing a tensile rupture strength of the metallic wire element of the radiotransparent coil;

a total increment of the tensile rupture strength being 8% or more due to the heat treatment at low temperature after finally drawn; and a relationship between X and Y being defined as follows:

$$Y \geq 1.777X + 70$$

where X (%) is the whole cross sectional reduction ratio, and Y (kgf/mm$^2$) is the tensile rupture strength represented by Y=P1/Sp, where P1 is a magnitude of a tensile force applied, and Sp is a cross sectional area of the metallic wire element when the metallic wire element surrenders to disconnection.

4. The medical guide wire according to any one of claims 1-3, wherein the metallic wire element of the radiotransparent coil is made of a re-melted austenitic stainless steel wire, melting heat of the welding member increasing a tensile rupture strength of the metallic wire element of the radiotransparent coil.

5. The medical guide wire according to claim 1, wherein the eutectic alloy of the welding member is an alloy of 80% gold and 20% tin by weight with a melting temperature as 280° C. or an alloy of 3.5% silver and 96.5% tin by weight with a melting temperature as 221° C., melting heat of the welding member increasing a tensile rupture strength of the metallic wire element of the radiotransparent coil.

6. The medical guide wire according to claim 1, wherein the core wire and the radiotransparent coil are bonded in part by the welding member to form a bonded portion in which one doughnut-shaped ring body or a plurality of doughnut-shaped ring bodies are provided from the distal end side to the proximal end side of the helical spring body with an outer diameter of the doughnut-shaped ring body ranging from 0.228 mm to 0.480 mm with a thickness ranging from 0.3 mm to 1.5 mm, or one doughnut-shaped ring body is provided at a proximal end portion of the helical spring body with an outer diameter of the doughnut-shaped ring body ranging from 0.228 mm to 0.480 mm with a thickness ranging from 0.3 mm to 3.0 mm, or a cone-shaped body is provided in a tapered-off fashion at the proximal end side of the helical spring body, melting heat of the welding member increasing a tensile rupture strength of the metallic wire element of the radiotransparent coil.

7. The medical guide wire according to claim 1, wherein an inner helical spring body is concentrically provided between the core wire and the helical spring body, the inner helical spring body being made of the radiotransparent coil diametrically reduced, the inner helical spring body is made from a plurality of the metallic wire elements stranded to form a wire-twisted hollow body, the core wire is bonded to the helical spring body or the inner helical spring body by the welding member to form a bonded portion in which a torus-shaped body or doughnut-shaped ring body is provided from the distal end side to the proximal end side of the helical spring body or the inner helical spring body with an outer diameter of the torus-shaped body or the doughnut-shaped ring body ranging from 0.228 mm to 0.480 mm with a thickness ranging from 0.3 mm to 1.5 mm, melting heat of the welding member increasing a tensile rupture strength of the metallic wire element of the radiotransparent coil.

8. The medical guide wire according to claim 1, wherein the helical spring body is heat treated at low temperature to form a synthetic resin layer on an outer surface of the helical spring body at the temperature of 180° C.-450° C. so as to generate a predetermined amount of conductive heat, the predetermined amount of conductive heat being conveyed from the synthetic resin layer to the metallic wire element of the radiotransparent coil, the synthetic resin layer having $2.5 \times 10^{-4}$ {cal/(cm·sec·°C.)} or more as a thermal conductivity at normal temperature, the heat treating at low temperature increasing a tensile rupture strength of the metallic wire element of the radiotransparent coil, and the metallic wire element having 15 (W·m$^{-1}$·K$^{-1}$) or more as a heat conductivity at normal temperature with the whole cross sectional reduction ratio as 90%-99.5%.

9. The medical guide wire according to claim 1, wherein the helical spring body is heat treated at low temperature to generate a predetermined amount of conductive heat from the welding member melted when the core wire and the helical spring body are in part bonded, while forming a synthetic resin layer on an outer surface of the helical spring body at the temperature of 180° C.-450° C. so as to generate a predetermined amount of conductive heat, the predetermined amount of conductive heat being conveyed from the synthetic resin layer and the eutectic alloy of the welding member to the metallic wire element of the radiotransparent coil, the eutectic alloy having 63 (W·m$^{-1}$·K$^{-1}$) or more as a heat conductivity at normal temperature, the synthetic resin layer having $2.5 \times 10^{-4}$ {cal/(cm·sec·°C.)} or more as a thermal conductivity at normal temperature, and the metallic wire element having 15 (W·m$^{-1}$·K$^{-1}$) or more as a heat conductivity at normal temperature with the whole cross sectional reduction ratio as 90%-99.5%, the heat treating at low temperature increasing a tensile rupture strength of the metallic wire element of the radiotransparent coil.

10. The medical guide wire according to claim 1, wherein a distal end side of the helical spring body has a radiopaque coil and a proximal end side of the helical spring body has a radiotransparent coil, the helical spring body is heat treated to generate a predetermined amount of conductive heat due to a melting heat concurrently produced when the radiopaque coil and the radiotransparent coil are in part bonded, while forming a synthetic resin layer on an outer surface of the helical spring body at the temperature of 180° C.-450° C. so as to generate a predetermined amount of conductive heat, the predetermined amount of conductive heat being conveyed from the eutectic alloy of the welding member, the synthetic resin layer and the radiopaque coil to the metallic wire element of the radiotransparent coil, the eutectic alloy having 63 $(W \cdot m^{-1} \cdot K^{-1})$ or more as a heat conductivity at normal temperature, the synthetic resin layer having $2.5 \times 10^{-4}$ {cal/(cm·sec·° C.)} or more as a thermal conductivity at normal temperature, the radiopaque coil having a heat conductivity four times or more than that of the radiotransparent coil at normal temperature, and the metallic wire element having 15 $(W \cdot m^{-1} \cdot K^{-1})$ or more as a heat conductivity at normal temperature with the whole cross sectional reduction ratio as 90%-99.5%, the heat treating at low temperature increasing a tensile rupture strength of the metallic wire element of the radiotransparent coil.

11. An assembly of a microcatheter and a guiding catheter combined with the medical guide wire according to any one of claims 1-3 and 5-10, wherein an outer diameter of the medical guide wire measures 0.228 mm-0.457 mm (0.009 inches-0.018 inches) which is inserted into the microcatheter, an inner diameter of which measures 0.28 mm-0.90 mm, and the medical guide wire inserted into the microcatheter is further inserted into the guiding catheter, an inner diameter of which ranges 1.91 mm to 2.67 mm, and the microcatheter forms a helical tube body provided by alternately winding or stranding a plurality of thick wires and thin wires, so that the helical tube body forms a concave-convex portion at an outer surface of the thick wires and the thin wires at least within 300 mm from a distal end of the helical tube body due to an exterior pressure or a pushing force at the time of inserting the helical tube body into a diseased area within a somatic cavity, melting heat of the welding member or heat treating at low temperature increasing a tensile rupture strength of the metallic wire element of the radiotransparent coil.

12. An assembly of a balloon catheter and a guiding catheter combined with the medical guide wire according to any one of claims 1-3 and 5-10, wherein an outer diameter of the medical guide wire measures 0.228 mm-0.254 mm (0.009 inches-0.018 inches) which is inserted into the balloon catheter, an inner diameter of which measures 0.28 mm-0.90 mm, and two pairs of the medical guide wire and the balloon catheter are inserted into the guiding catheter, an inner diameter of which measures 1.91 mm-2.67 mm so as to enable a user to readily handle a kissing operation, melting heat of the welding member or the heat treating at low temperature increasing a tensile rupture strength of the metallic wire element of the radiotransparent coil.

\* \* \* \* \*